United States Patent
Levey et al.

(10) Patent No.: US 9,758,809 B2
(45) Date of Patent: Sep. 12, 2017

(54) RNA SPLICING ALTERATIONS AND U1 SMALL NUCLEAR RIBONUCLEOPROTEINS IN NEURODEGENERATIVE DISEASES

(71) Applicant: EMORY UNIVERSITY, Atlanta, GA (US)

(72) Inventors: Allan I Levey, Atlanta, GA (US); Junmin Peng, Memphis, TN (US); James Lah, Avondale Estates, GA (US); Bing Bai, Memphis, TN (US); Chadwick McKinley Hales, Atlanta, GA (US); Ping-Chung Chen, Memphis, TN (US); Nicholas Thomas Seyfried, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 14/199,456

(22) Filed: Mar. 6, 2014

(65) Prior Publication Data

US 2014/0255927 A1    Sep. 11, 2014

Related U.S. Application Data

(60) Provisional application No. 61/773,227, filed on Mar. 6, 2013.

(51) Int. Cl.
| | | |
|---|---|---|
| *C12Q 1/00* | (2006.01) | |
| *G01N 33/53* | (2006.01) | |
| *G01N 33/542* | (2006.01) | |
| *C12Q 1/68* | (2006.01) | |
| *G01N 33/68* | (2006.01) | |

(52) U.S. Cl.
CPC .............. *C12Q 1/68* (2013.01); *C12Q 1/6883* (2013.01); *G01N 33/6875* (2013.01); *G01N 33/6896* (2013.01); *C12Q 2600/158* (2013.01); *G01N 2560/00* (2013.01); *G01N 2800/2821* (2013.01)

(58) Field of Classification Search
None
See application file for complete search history.

(56) References Cited

PUBLICATIONS

Bai et al. "U1 small nuclear ribonucleoprotein complex and RNA splicing alterations in Alzheimer's disease" PNAS, 2013; 110(41): 16562-16567.
Fujiwara et al. "Alpha-synuclein is phosphorylated in synucleinopathy lesions" Nat Cell Biol, 2002; 4(2):160-164.
Kaida et al. "U1 snRNP protects pre-mRNAs from premature cleavage and polyadenylation" Nature, 2010; 468*7324): 664-668.
Neumann et al. "Ubiquitinated TDP-43 in frontotemporal lobar degeneration and amyotrophic lateral sclerosis" Science, 2006; 314(5796): 130-133.
Spillantini et al. "Familial multiple system tauopathy with presenile dementia: A disease with abundant neuronal and glial tau filaments" Proc Natl Acad Sci USA, 1997; 94(8): 4113-4118.

*Primary Examiner* — Olga N Chernyshev
(74) *Attorney, Agent, or Firm* — Emory Patent Group

(57) ABSTRACT

This disclosure relates to methods of diagnosing neurodegenerative disease by analyzing proteins or protein expression profiles in a subject, or RNA or RNA expression profiles in a subject. In certain embodiments, the disclosure contemplates the diagnosis of preclinical or symptomatic stages of Alzheimer's disease, mild cognitive impairment, or chronic traumatic encephalopathy by identification of components of U1 small nuclear ribonucleoproteins or fragments thereof which are capable of forming cytoplasmic tangle-like structures.

9 Claims, 11 Drawing Sheets

SEQUENCE LISTING

```
<160> NUMBER OF SEQ ID NOS: 10

<210> SEQ ID NO 1
<211> LENGTH: 19
<212> TYPE: DNA
<213> ORGANISM: Homo sapiens

<400> SEQUENCE: 1
gccguacauu cgagaguuu                                                    19

<210> SEQ ID NO 2
<211> LENGTH: 19
<212> TYPE: DNA
<213> ORGANISM: Homo sapiens

<400> SEQUENCE: 2
acacgcagau ggcaagaag                                                    19

<210> SEQ ID NO 3
<211> LENGTH: 19
<212> TYPE: RNA
<213> ORGANISM: Homo sapiens

<400> SEQUENCE: 3
uacacauggu cuacaguaa                                                    19

<210> SEQ ID NO 4
<211> LENGTH: 19
<212> TYPE: DNA
<213> ORGANISM: Homo sapiens

<400> SEQUENCE: 4
gagagugaau uaugacaca                                                    19

<210> SEQ ID NO 5
<211> LENGTH: 19
<212> TYPE: DNA
<213> ORGANISM: Homo sapiens

<400> SEQUENCE: 5
ugguuuacau gucgacuaa                                                    19

<210> SEQ ID NO 6
<211> LENGTH: 22
<212> TYPE: PRT
<213> ORGANISM: Homo sapiens

<400> SEQUENCE: 6

Gly Asp Ala Phe Lys Thr Leu Phe Val Ala Arg Val Asn Tyr Asp Thr
1               5                   10                  15

Thr Glu Ser Lys Leu Arg
            20

<210> SEQ ID NO 7
<211> LENGTH: 19
<212> TYPE: PRT
<213> ORGANISM: Homo sapiens

<400> SEQUENCE: 7

Gly Gly Asp Gly Tyr Leu Ala Pro Glu Asn Gly Tyr Leu Met Glu Ala
1               5                   10                  15

Ala Pro Glu
```

<210> SEQ ID NO 8
<211> LENGTH: 1922
<212> TYPE: PRT
<213> ORGANISM: Homo sapiens

<400> SEQUENCE: 8

```
Gly Cys Gly Gly Thr Thr Cys Gly Gly Cys Gly Gly Ala Ala
1               5                   10                  15

Ala Gly Cys Gly Gly Gly Ala Gly Gly Thr Gly Ala Gly Gly
            20                  25                  30

Gly Cys Gly Gly Cys Thr Thr Gly Gly Gly Cys Ala Ala Gly Cys
            35                  40                  45

Gly Cys Gly Cys Gly Cys Gly Cys Cys Ala Gly Thr Gly Cys Ala
            50                  55                  60

Gly Ala Ala Gly Cys Cys Ala Cys Cys Cys Cys Gly Cys
65                  70                  75                  80

Gly Gly Cys Thr Gly Ala Gly Gly Thr Ala Cys Thr Cys Ala Ala Gly
                85                  90                  95

Gly Thr Gly Cys Cys Cys Ala Ala Gly Gly Cys Gly Gly Gly
            100                 105                 110

Thr Ala Gly Thr Gly Ala Cys Cys Thr Cys Cys Gly Gly Thr
            115                 120                 125

Gly Cys Gly Cys Thr Gly Thr Gly Cys Cys Gly Cys Gly Gly Cys
            130                 135                 140

Ala Gly Cys Gly Cys Cys Gly Gly Gly Thr Cys Cys Thr Ala Gly Thr
145                 150                 155                 160

Gly Thr Gly Thr Gly Gly Gly Thr Thr Gly Thr Gly Thr Thr Gly
                165                 170                 175

Gly Cys Ala Cys Cys Gly Cys Ala Cys Gly Gly Cys Gly Cys Gly Thr
                180                 185                 190

Gly Cys Gly Cys Ala Gly Thr Gly Ala Gly Gly Ala Cys Gly Gly Cys
            195                 200                 205

Gly Gly Ala Gly Gly Gly Ala Thr Thr Thr Gly Cys Gly Gly Cys Cys
            210                 215                 220

Gly Gly Gly Ala Cys Cys Cys Ala Cys Cys Cys Cys Thr Gly Cys
225                 230                 235                 240

Thr Cys Cys Ala Gly Thr Cys Gly Cys Thr Ala Thr Cys Gly Gly Ala
                245                 250                 255

Gly Gly Cys Cys Gly Cys Gly Cys Gly Gly Gly Thr Gly Gly Cys Thr
            260                 265                 270

Gly Ala Gly Cys Ala Gly Cys Gly Gly Cys Cys Thr Gly Gly Thr
            275                 280                 285

Cys Gly Cys Thr Cys Gly Cys Thr Thr Ala Gly Cys Gly Gly Gly Cys
            290                 295                 300

Gly Ala Cys Gly Gly Ala Ala Thr Cys Ala Gly Ala Cys Gly Gly Ala
305                 310                 315                 320

Cys Gly Thr Gly Gly Ala Cys Gly Cys Cys Cys Cys Gly Gly Ala
                325                 330                 335

Gly Thr Gly Gly Ala Ala Gly Cys Cys Gly Ala Ala Gly Cys Ala Gly
            340                 345                 350

Gly Ala Gly Thr Thr Gly Thr Thr Gly Thr Thr Gly Cys Thr Gly Ala
                355                 360                 365

Gly Gly Gly Gly Cys Thr Gly Cys Cys Gly Cys Cys Gly Cys Cys Gly
            370                 375                 380
```

```
Cys Cys Gly Cys Gly Ala Cys Cys Thr Cys Gly Gly Ala Cys
385                 390             395             400

Ala Gly Ala Cys Gly Cys Ala Gly Ala Cys Gly Ala Gly Gly
            405             410             415

Ala Gly Gly Gly Cys Gly Cys Thr Ala Cys Gly Cys Ala Cys Thr
                420             425             430

Thr Gly Gly Cys Ala Ala Gly Ala Thr Gly Ala Cys Cys Ala Gly
            435             440             445

Thr Thr Cys Cys Thr Gly Cys Cys Gly Cys Cys Ala Ala Cys Cys
            450             455             460

Thr Thr Cys Thr Gly Gly Cys Cys Cys Thr Cys Thr Thr Gly Cys
465             470             475             480

Cys Cys Cys Cys Cys Gly Thr Gly Ala Cys Cys Thr Ala Thr Thr
                485             490             495

Cys Cys Ala Thr Ala Cys Cys Thr Gly Cys Cys Ala Cys Cys Cys
            500             505             510

Thr Gly Gly Ala Gly Ala Ala Ala Cys Thr Gly Cys Cys Ala Cys Ala
        515             520             525

Thr Gly Ala Ala Ala Ala Cys Ala Cys Cys Ala Cys Ala Ala Thr
        530             535             540

Cys Ala Ala Cys Cys Thr Thr Ala Thr Thr Gly Thr Gly Gly Cys Ala
545             550             555             560

Thr Thr Gly Cys Gly Cys Cys Gly Thr Ala Cys Ala Thr Thr Cys Gly
            565             570             575

Ala Gly Ala Gly Thr Thr Thr Gly Ala Gly Gly Ala Cys Cys Cys Thr
            580             585             590

Cys Gly Ala Gly Ala Thr Gly Cys Cys Cys Thr Cys Cys Thr Cys
            595             600             605

Cys Ala Ala Cys Thr Cys Gly Thr Gly Cys Thr Gly Ala Ala Ala Cys
            610             615             620

Cys Cys Gly Ala Gly Ala Gly Gly Ala Gly Cys Gly Cys Ala Thr Gly
625             630             635             640

Gly Ala Gly Ala Gly Gly Ala Ala Ala Ala Gly Ala Cys Gly Gly Gly
            645             650             655

Ala Ala Ala Ala Gly Ala Thr Thr Gly Ala Gly Cys Gly Gly Cys Gly
            660             665             670

Ala Cys Ala Gly Cys Ala Ala Gly Ala Ala Gly Thr Gly Gly Ala Gly
            675             680             685

Ala Cys Ala Gly Ala Gly Cys Thr Thr Ala Ala Ala Thr Gly Thr
            690             695             700

Gly Gly Gly Ala Cys Cys Cys Thr Cys Ala Cys Ala Ala Thr Gly Ala
705             710             715             720

Thr Cys Cys Cys Ala Ala Thr Gly Cys Thr Cys Ala Gly Gly Gly Gly
            725             730             735

Gly Ala Thr Gly Cys Cys Thr Thr Cys Ala Ala Gly Ala Cys Thr Cys
            740             745             750

Thr Cys Thr Thr Cys Gly Thr Gly Gly Cys Gly Ala Gly Ala Gly Thr
            755             760             765

Gly Ala Ala Thr Thr Ala Thr Gly Ala Cys Ala Cys Ala Ala Cys Ala
            770             775             780

Gly Ala Ala Thr Cys Cys Ala Ala Gly Cys Thr Cys Cys Gly Gly Ala
785             790             795             800
```

-continued

Gly Ala Gly Ala Gly Thr Thr Thr Gly Ala Gly Thr Gly Thr Ala
                    805                 810                 815

Cys Gly Gly Ala Cys Cys Thr Ala Thr Cys Ala Ala Ala Gly Ala
                820                 825                 830

Ala Thr Ala Cys Ala Cys Ala Thr Gly Thr Cys Thr Ala Cys Ala
            835                 840                 845

Gly Thr Ala Ala Gly Cys Gly Thr Cys Ala Gly Gly Ala Ala Ala
        850                 855                 860

Gly Cys Cys Cys Cys Gly Thr Gly Gly Cys Thr Ala Thr Gly Cys Cys
865                 870                 875                 880

Thr Thr Cys Ala Thr Cys Gly Ala Gly Thr Ala Cys Gly Ala Ala Cys
            885                 890                 895

Ala Cys Gly Ala Gly Cys Gly Ala Gly Ala Cys Ala Thr Gly Cys Ala
        900                 905                 910

Cys Thr Cys Cys Gly Cys Thr Thr Ala Cys Ala Ala Ala Cys Ala Cys
            915                 920                 925

Gly Cys Ala Gly Ala Thr Gly Gly Cys Ala Ala Gly Ala Ala Gly Ala
        930                 935                 940

Thr Thr Gly Ala Thr Gly Gly Cys Ala Gly Gly Ala Gly Gly Gly Thr
945                 950                 955                 960

Cys Cys Thr Thr Gly Thr Gly Ala Cys Gly Thr Gly Gly Ala Gly
                965                 970                 975

Ala Gly Gly Gly Cys Cys Gly Ala Ala Cys Cys Gly Thr Gly Ala
                980                 985                 990

Ala Gly Gly Gly Cys Thr Gly Gly Ala Gly Gly Cys Cys Cys Cys Gly
        995                 1000                1005

Gly Cys Gly Gly Cys Thr Ala Gly Gly Ala Gly Gly Ala Gly Gly
    1010                1015                1020

Cys Cys Thr Cys Gly Gly Thr Gly Gly Thr Ala Cys Cys Ala Gly
    1025                1030                1035

Ala Ala Gly Ala Gly Gly Ala Gly Gly Gly Gly Cys Thr Gly Ala
    1040                1045                1050

Thr Gly Thr Gly Ala Ala Cys Ala Thr Cys Cys Gly Gly Cys Ala
    1055                1060                1065

Thr Thr Cys Ala Gly Gly Cys Cys Gly Cys Gly Ala Thr Gly Ala
    1070                1075                1080

Cys Ala Cys Cys Thr Cys Cys Cys Gly Cys Thr Ala Cys Gly Ala
    1085                1090                1095

Thr Gly Ala Gly Ala Gly Gly Cys Cys Cys Gly Gly Cys Cys Cys
    1100                1105                1110

Cys Thr Cys Cys Cys Cys Gly Cys Thr Thr Cys Cys Gly Cys Ala
    1115                1120                1125

Cys Ala Gly Gly Gly Ala Cys Cys Gly Gly Gly Ala Cys Cys Gly
    1130                1135                1140

Gly Gly Ala Cys Cys Gly Thr Gly Ala Gly Cys Gly Gly Gly Ala
    1145                1150                1155

Gly Cys Gly Cys Ala Gly Ala Gly Ala Gly Cys Gly Gly Ala Gly
    1160                1165                1170

Cys Cys Gly Gly Gly Ala Gly Cys Gly Ala Gly Ala Cys Ala Ala
    1175                1180                1185

Gly Gly Ala Gly Cys Gly Ala Gly Ala Ala Cys Gly Gly Cys Gly
    1190                1195                1200

Ala Cys Gly Cys Thr Cys Cys Cys Gly Cys Thr Cys Cys Cys Gly

-continued

```
            1205                1210                1215
Gly Gly Ala Cys Cys Gly Gly Cys Gly Gly Ala Gly Gly Cys Gly
            1220                1225                1230
Cys Thr Cys Ala Cys Gly Gly Ala Gly Thr Cys Gly Cys Gly Ala
            1235                1240                1245
Cys Ala Ala Gly Gly Ala Gly Gly Ala Gly Cys Gly Gly Ala Gly
            1250                1255                1260
Gly Cys Gly Cys Thr Cys Cys Ala Gly Gly Ala Gly Cys Gly
            1265                1270                1275
Gly Ala Gly Cys Ala Ala Gly Gly Ala Cys Ala Ala Gly Gly Ala
            1280                1285                1290
Cys Cys Gly Gly Gly Ala Cys Cys Gly Gly Ala Ala Gly Cys Gly
            1295                1300                1305
Gly Cys Gly Gly Ala Ala Gly Cys Ala Gly Cys Cys Gly Gly Ala Gly
            1310                1315                1320
Thr Cys Gly Gly Gly Ala Gly Cys Gly Gly Gly Cys Cys Cys Gly
            1325                1330                1335
Gly Cys Gly Gly Gly Ala Gly Cys Gly Gly Gly Ala Gly Cys Gly
            1340                1345                1350
Cys Ala Ala Gly Gly Ala Gly Gly Ala Gly Cys Thr Gly Cys Gly
            1355                1360                1365
Thr Gly Gly Cys Gly Gly Cys Gly Gly Thr Gly Gly Cys Gly Ala
            1370                1375                1380
Cys Ala Thr Gly Gly Cys Gly Gly Ala Gly Cys Cys Cys Thr Cys
            1385                1390                1395
Cys Gly Ala Gly Gly Cys Gly Gly Gly Thr Gly Ala Cys Gly Cys
            1400                1405                1410
Gly Cys Cys Cys Cys Cys Thr Gly Ala Thr Gly Ala Thr Gly Gly
            1415                1420                1425
Gly Cys Cys Thr Cys Cys Ala Gly Gly Gly Gly Ala Gly Cys Thr
            1430                1435                1440
Cys Gly Gly Gly Cys Cys Thr Gly Ala Cys Gly Gly Cys Cys Cys
            1445                1450                1455
Thr Gly Ala Cys Gly Gly Thr Cys Cys Ala Gly Ala Gly Gly Ala
            1460                1465                1470
Ala Ala Ala Gly Gly Gly Cys Cys Gly Gly Ala Thr Cys Gly
            1475                1480                1485
Thr Gly Ala Cys Cys Gly Gly Gly Ala Gly Cys Gly Ala Cys Gly
            1490                1495                1500
Gly Cys Gly Gly Ala Gly Cys Cys Ala Cys Cys Gly Gly Ala Gly
            1505                1510                1515
Cys Gly Ala Gly Cys Gly Cys Gly Ala Gly Cys Gly Gly Cys Gly
            1520                1525                1530
Cys Cys Gly Gly Gly Ala Cys Cys Gly Gly Ala Thr Cys Gly
            1535                1540                1545
Thr Gly Ala Cys Cys Gly Thr Gly Ala Cys Cys Gly Thr Gly Ala
            1550                1555                1560
Cys Cys Gly Cys Gly Ala Gly Cys Ala Cys Ala Ala Cys Gly
            1565                1570                1575
Gly Gly Gly Gly Gly Ala Gly Cys Gly Gly Gly Cys Ala Gly
            1580                1585                1590
Thr Gly Ala Gly Cys Gly Gly Gly Gly Cys Ala Gly Gly Gly Ala
            1595                1600                1605
```

Thr Gly Ala Gly Gly Cys Cys Cys Gly Ala Gly Thr Gly Gly
    1610                1615                1620

Gly Gly Gly Cys Gly Gly Thr Gly Gly Cys Ala Gly Gly Ala
    1625                1630                1635

Cys Ala Ala Cys Gly Gly Gly Cys Thr Gly Gly Ala Gly Gly
    1640                1645                1650

Thr Cys Thr Gly Gly Gly Cys Ala Ala Cys Gly Ala Cys Ala Gly
    1655                1660                1665

Cys Cys Gly Ala Gly Ala Cys Ala Thr Gly Thr Ala Cys Ala Thr
    1670                1675                1680

Gly Gly Ala Gly Thr Cys Thr Gly Ala Gly Gly Cys Gly Gly
    1685                1690                1695

Cys Gly Ala Cys Gly Gly Cys Thr Ala Cys Cys Thr Gly Gly Cys
    1700                1705                1710

Thr Cys Cys Gly Gly Ala Gly Ala Ala Thr Gly Gly Gly Thr Ala
    1715                1720                1725

Thr Thr Thr Gly Ala Thr Gly Gly Ala Gly Gly Cys Thr Gly Cys
    1730                1735                1740

Gly Cys Cys Gly Gly Ala Gly Thr Gly Ala Ala Gly Ala Gly Gly
    1745                1750                1755

Thr Cys Gly Thr Cys Cys Thr Cys Thr Cys Cys Ala Thr Cys Thr
    1760                1765                1770

Gly Cys Thr Gly Thr Gly Thr Thr Thr Gly Gly Ala Cys Gly Cys
    1775                1780                1785

Gly Thr Thr Cys Cys Thr Gly Cys Cys Cys Ala Gly Cys Cys Cys
    1790                1795                1800

Cys Thr Thr Gly Cys Thr Gly Thr Cys Ala Thr Cys Cys Cys Cys
    1805                1810                1815

Thr Cys Cys Cys Cys Ala Ala Cys Cys Thr Thr Gly Gly Cys
    1820                1825                1830

Cys Ala Cys Thr Thr Gly Ala Gly Thr Thr Thr Gly Thr Cys Cys
    1835                1840                1845

Thr Cys Cys Ala Ala Gly Gly Gly Thr Ala Gly Gly Thr Gly Thr
    1850                1855                1860

Cys Thr Cys Ala Thr Thr Thr Gly Thr Thr Cys Thr Gly Gly Cys
    1865                1870                1875

Cys Cys Cys Thr Thr Gly Gly Ala Thr Thr Thr Ala Ala Ala Ala
    1880                1885                1890

Ala Thr Ala Ala Ala Ala Thr Thr Ala Ala Thr Thr Thr Cys Cys
    1895                1900                1905

Thr Gly Thr Thr Gly Ala Thr Ala Gly Thr Gly Gly Gly Cys
    1910                1915                1920

<210> SEQ ID NO 9
<211> LENGTH: 22
<212> TYPE: PRT
<213> ORGANISM: Homo sapiens

<400> SEQUENCE: 9

Gly Asp Ala Phe Lys Thr Leu Phe Val Ala Arg Val Asn Tyr Asp Thr
1               5                   10                  15

Thr Glu Ser Lys Leu Arg
            20

```
<210> SEQ ID NO 10
<211> LENGTH: 19
<212> TYPE: PRT
<213> ORGANISM: Homo sapiens

<400> SEQUENCE: 10

Gly Gly Asp Gly Tyr Leu Ala Pro Glu Asn Gly Tyr Leu Met Glu Ala
1               5                   10                  15

Ala Pro Glu
```

RNA SPLICING ALTERATIONS AND U1 SMALL NUCLEAR RIBONUCLEOPROTEINS IN NEURODEGENERATIVE DISEASES

CROSS REFERENCE TO RELATED APPLICATIONS

This application claims the benefit of U.S. Provisional Application No. 61/773,227 filed Mar. 6, 2013. The entirety of this application is hereby incorporated by reference for all purposes.

STATEMENT REGARDING FEDERALLY FUNDED RESEARCH

This invention was made with government support under Grant P50AG025688, P30NS 055077, and P50AG005136 awarded by the National Institutes of Health. The government has certain rights in the invention.

BACKGROUND

Deposition of insoluble protein aggregates in the brain is a hallmark of many neurodegenerative diseases. Identification of the aggregated proteins provides insights into molecular pathogenesis. Beta-amyloid (Aβ) and tau aggregates are typically found in Alzheimer disease (AD). Alpha-synuclein in Lewy bodies is typically found in Parkinson disease (PD). Ubiquitin-positive, tau- and α-synuclein-negative inclusions are typical of frontotemporal lobar degeneration with ubiquitin-positive inclusions generally referred to as ubiquitin-positive frontotemporal lobar degeneration (FTLD-U). Ubiquitinated TDP-43 is found in frontotemporal lobar degeneration and amyotrophic lateral sclerosis (ALS). In AD, the amyloid cascade hypothesis and tau hypothesis dominate pathogenesis research. However, there is a need to further understand underlying etiology of the disease.

Mature messenger RNAs are derived from primary transcripts (pre-mRNAs) and undergo post-transcriptional processing such as 5' end capping, removal of introns by splicing, and polyadenylation. Spliceosomes are RNA and protein complexes that catalyze splicing reactions. U1 small nuclear ribonucleoprotein (snRNP) is found in spliceosomes and expressed in humans. Functional U1 snRNP knockdown results in accumulated unspliced pre-mRNAs by genomic tiling microarrays. See Kaida et al., Nature, 2010, 468, 664-668.

SUMMARY

This disclosure relates to methods of diagnosing neurodegenerative disease by analyzing proteins, RNAs, or protein expression profiles in a subject. In certain embodiments, the disclosure contemplates the diagnosis of Alzheimer's disease by identification of U1 small nuclear ribonucleoproteins or fragments thereof, and associated molecules, which are capable of forming cytoplasmic tangle-like structures.

In certain embodiments, the disclosure contemplates methods of diagnosing a neurodegenerative disease comprising evaluating a sample from a subject for altered expression of ribonucleoprotein components, e.g., a protein or RNA, and diagnosing a neurodegenerative disease based on the altered expression the components, e.g., wherein the ribonucleoprotein is a U1 small nuclear ribonucleoprotein.

In certain embodiments, the disclosure contemplates that the sample is brain tissue. In certain embodiments, the disclosure contemplates that the test sample is a human CSF sample. Typically, the CSF sample is manipulated, e.g., by filtration, to remove albumin prior to measuring levels of one or more ribonucleoprotein components. Typically, one compares a normalized level of the components to the level in a test sample. If the ribonucleoprotein components vary from a normalized level when compared to the test sample in a statistically significant way, then the subject is diagnosed with, suspected of having, or will be monitored, or treated for Alzheimer's disease (AD).

For example, in one embodiment, methods disclosed herein are indicative of AD, in a subject at risk of or exhibiting symptoms of AD, and thereafter CSF analysis for amyloid and tau measurements are performed.

For example, in one embodiment, methods disclosed herein are indicative of AD, in a subject at risk of or exhibiting symptoms of AD, and thereafter an imaging agent such as florbetapir ($^{18}$F) and/or a therapeutic agent related to treating or ameliorating one or more symptoms of AD are administered to the subject, such as the administration of medications for memory loss, treatments for behavioral changes, treatments for sleep changes. Such medication may be selected from cholinesterase inhibitors such as donepezil, rivastigmine, galantamine, and tacrine and/or an agent for blocking NMDA receptor such as memantine to treat the cognitive symptoms (memory loss, confusion, and problems with thinking and reasoning) of Alzheimer's disease. Other medications include Vitamin E. Other medications include anti-irritability, anti-anxiety, anti-psychotic, anti-insomnia, and anti-depression agents. Contemplated agents also include monoclonal antibody vaccines to amyloid including but not limited to solanuzemab, gantenerumab, and bapineuzumab.

In certain embodiments, the method further comprises the step of recording the altered expression or diagnosis on a computer readable medium. In certain embodiments, the method further comprises the step of reporting the diagnosis or altered expression to a medical professional or the subject.

In certain embodiments, the ribonucleoprotein components, e.g., protein or RNA, are U1 small nuclear ribonucleoprotein is human U1-70K (U1 small nuclear ribonucleoprotein 70 kDa), 40 kD N-terminal fragment of U1-70K, or U1 small nuclear ribonucleoprotein A (U1A), U5 small nuclear ribonucleoprotein 200 kDa helicase, U4/U6.U5 small nuclear ribonucleoprotein 27 kDa protein, U5 small nuclear ribonucleoprotein 40 kDa protein, small nuclear ribonucleoprotein-associated proteins B and B' isoform B, U1 small nuclear ribonucleoprotein C, small nuclear ribonucleoprotein Sm D1, small nuclear ribonucleoprotein Sm D2 isoform 1, small nuclear ribonucleoprotein Sm D3, small nuclear ribonucleoprotein E, small nuclear ribonucleoprotein F, small nuclear ribonucleoprotein G, small nuclear ribonucleoprotein N, splicing factor U2AF 35 kDa subunit isoform a, splicing factor U2AF 65 kDa subunit isoform b, U2 snRNP-associated SURP motif-containing protein, putative RNA-binding protein Luc7-like 2 isoform 1, luc7-like protein 3, probable ATP-dependent RNA helicase DDX46, probable ATP-dependent RNA helicase DDX5, protein LSM2, protein LSM3, protein LSM4, protein LSM5, protein LS6, protein LSM7, splicing factor 3A subunit 1 isoform 1, splicing factor 3A subunit 3, splicing factor 3B subunit 1 isoform 1, pre-mRNA branch site protein p14, splicing factor 3B subunit 3, poly(U)-binding-splicing factor PUF60, probable ATP-dependent RNA helicase DDX23, U1 snRNA, U2 snRNA, U5 snRNA, U4/U6, snRNA, U6 snRNA, serine/arginine repetitive matrix protein 1, serine/arginine repetitive matrix protein 2, serine/arginine-rich splicing factor 1 isoform 1, serine/arginine-rich splicing factor 10 isoform 1, serine/arginine-rich splicing factor 11 isoform 1, serine/arginine-rich splicing factor 12, serine/arginine-rich splicing factor 2, serine/arginine-rich splicing factor 3, serine/arginine-rich splicing factor 4, serine/arginine-rich splicing factor 6, or combinations of thereof.

In certain embodiments, the U1 small nuclear ribonucleoprotein is U1 snRNA. In certain embodiments, the U1 small nuclear ribonucleoprotein is a protein that has a molecular association with one of the U1 snRNP proteins or snRNA. In certain embodiments, the neurodegenerative disease is Alzheimer disease, mild cognitive impairment, preclinical stages of Alzheimer's disease and mild cognitive impairment, and chronic traumatic encephalopathy.

In certain embodiments, the sample is of blood plasma, cerebrospinal fluid, or brain tissue. In certain embodiments, the sample is product of extracting the protein from blood plasma, cerebrospinal fluid, or brain tissue of the subject in an aqueous solution comprising a detergent at about or greater than 1% by weight providing a detergent soluble fraction and a detergent insoluble fraction. In certain embodiments, the sample is the detergent insoluble fraction wherein the altered expression is an increased in a U1 small nuclear ribonucleoprotein in the detergent insoluble fraction correlating to a diagnosis of preclinical or symptomatic Alzheimer disease, mild cognitive impairment, or chronic traumatic encephalopathy. In certain embodiments, the detergent is N-lauroyl-sarcosine.

In certain embodiments, the disclosure relates to using immunohistochemistry to detect cytoplasmic localization of small nuclear ribonucleoprotein components in preclinical or symptomatic AD, MCI, or chronic traumatic encephalopathy.

In certain embodiments, the altered expression is evaluated by purifying the protein by a chromatography method and measuring an amount of the U1 small nuclear ribonucleoprotein component(s) in the sample by mass spectrometry. In certain embodiments, the chromatography method is electrophoresis on a sodium dodecyl sulfate polyacrylamide gel or liquid chromatography. In certain embodiments, the altered expression is evaluated by measuring an amount of the U1 small nuclear ribonucleoprotein in the sample by an affinity marker or affinity chromatography. In certain embodiments, the affinity marker is an antibody using an immunoassay. In certain embodiments, the altered expression is evaluated by measuring an amount of RNA in the U1 small nuclear ribonucleoprotein. In certain embodiments, the altered expression is evaluated by measuring the hybridization of a probe to genomic DNA encoding the U1 small nuclear ribonucleoprotein. In certain embodiments, the probe is a fluorescent probe.

In certain embodiments, measuring expression is done by immunohistochemistry or quantifying and or measuring protein, RNA expression or nuclear DNA transcription by measuring the relative abundance of newly formed transcripts, detecting active transcription sites, measuring the total or nuclear RNA levels, measuring the presence of a transcript, incorporating RNA stem loops sequences into a gene and measuring incorporated the incorporated sequence synthesized RNA by binding a molecule that has a high affinity for sequence-specific interaction with the sequence, directing a fluorescent probe to the site of transcription and visualizing as a fluorescent spot, separating RNA by size such as by electrophoresis and detecting with a hybridization probe complementary to part of target sequence.

In certain embodiments, the method further comprises the step of evaluating the sample from a subject for altered expression of amyloid beta, microtubule-associated tau, and/or apolipoprotein E.

In certain embodiments, the disclosure relates to methods of diagnosing a neurodegenerative disease comprising evaluating a sample from a subject for altered expression of a protein, and diagnosing a neurodegenerative disease based on the altered expression the protein, wherein the protein is RNA helicase Prp5.

In certain embodiments, the disclosure relates to diagnosing Alzheimer disease, mild cognitive impairment, or chronic traumatic encephalopathy comprising evaluating the amount of pre-mRNA and mature mRNA from a sample of the subject and diagnosing Alzheimer disease, mild cognitive impairment or chronic traumatic encephalopathy based on the relative amounts of pre-mRNA and mature mRNA in the sample. In certain embodiments, the pre-mRNA and mature mRNA are of a protein selected from BIN1, CLU, and PSEN1. In certain embodiments, the method further comprises the step of recording the amount of pre-mRNA and mature mRNA, relative amounts, or diagnosis on a computer readable medium. In certain embodiments, the method further comprises the step of reporting the diagnosis, the amount of pre-mRNA and mature mRNA, or relative amounts to a medical professional or the subject. In certain embodiments, the amount of pre-mRNA is measured by the amount of mRNA with exon1 to intron1 in the sample. In certain embodiments, the amount of mature mRNA is measured by the amount of mRNA with exon1 to exon2 in the sample.

In certain embodiments, the disclosure relates to methods of diagnosing Alzheimer disease or mild cognitive impairment comprising evaluating a sample from a subject for altered expression of APP770, APP751, or APP695 and diagnosing Alzheimer disease or mild cognitive impairment based on the altered expression.

In certain embodiments, a decrease of APP770 indicates a diagnosis of Alzheimer disease or mild cognitive impairment. In certain embodiments, an increase of APP751 or APP695 indicates a diagnosis of Alzheimer disease or mild cognitive impairment. In certain embodiments, the method further comprises the step of recording the altered expression or diagnosis on a computer readable medium. In certain embodiments, the method further comprises the step of reporting the diagnosis or altered expression to a medical professional or the subject.

In certain embodiments, the disclosure relates to antibodies or antibody mimetics that bind to the epitopes/polypeptides comprising GDAFKTLFVARVNYDTTESKLR (SEQ ID NO: 6, N-terminal amino acid 99-120 of U1-70K), and GGDGYLAPENGYLMEAAPE (SEQ ID NO: 7, C-terminal amino acid 419 to 437 of U1-70K). In certain embodiments, the antibodies are monoclonal or polyclonal.

In certain embodiments, the disclosure relates to antibodies, antibody mimetics, or polynucleobase probes that bind to the epitopes or any stretch of polypeptide or nucleic acid sequences within U1 small nuclear ribonucleoprotein is human U1-70K (U1 small nuclear ribonucleoprotein 70 kDa), 40 kD N-terminal fragment of U1-70K, or U1 small nuclear ribonucleoprotein A (U1A), U5 small nuclear ribonucleoprotein 200 kDa helicase, U4/U6.U5 small nuclear ribonucleoprotein 27 kDa protein, U5 small nuclear ribonucleoprotein 40 kDa protein, small nuclear ribonucleoprotein-associated proteins B and B' isoform B, U1 small nuclear ribonucleoprotein C, small nuclear ribonucleoprotein Sm D1, small nuclear ribonucleoprotein Sm D2 isoform 1, small nuclear ribonucleoprotein Sm D3, small nuclear ribonucleoprotein E, small nuclear ribonucleoprotein F, small nuclear ribonucleoprotein G, small nuclear ribonucleoprotein N, splicing factor U2AF 35 kDa subunit isoform a, splicing factor U2AF 65 kDa subunit isoform b, U2 snRNP-associated SURP motif-containing protein, putative RNA-binding protein Luc7-like 2 isoform 1, luc7-like protein 3, probable ATP-dependent RNA helicase DDX46, probable ATP-dependent RNA helicase DDX5, protein LSM2, protein LSM3, protein LSM4, protein LSM5, protein LS6, protein LSM7, splicing factor 3A subunit 1 isoform 1, splicing factor 3A subunit 3, splicing factor 3B subunit 1 isoform 1, pre-mRNA branch site protein p14, splicing factor 3B subunit 3, poly(U)-binding-splicing factor PUF60, probable ATP-dependent RNA helicase DDX23, U1 snRNA, U2 snRNA, U5 snRNA, U4/U6, snRNA, U6 snRNA, serine/arginine repetitive matrix protein 1, serine/arginine repetitive matrix protein 2, serine/arginine-rich splicing factor 1 isoform 1, serine/arginine-rich splicing factor 10 isoform 1, serine/arginine-rich splicing factor 11 isoform 1, serine/arginine-rich splicing factor 12, serine/arginine-rich splicing factor 2, serine/arginine-rich splicing factor 3, serine/arginine-rich splicing factor 4, or serine/arginine-rich splicing factor 6 as the sequences are provided for *homo sapiens* in NCBI protein and nucleotide database National Center for Biotechnology information, hereby incorporated by reference.

In certain embodiments, this disclosure contemplate methods of treating or preventing AD by administering an effective amount of a compound that binds the LC1 domain (amino acids 231-308) of human U1-70K to a subject in need thereof. In certain embodiments, the compound is an antibody or antibody mimetic. In certain embodiments, the compound is administered intracranially, e.g., by convention enhanced delivery.

In certain embodiments, the disclosure contemplates the treatment or prevention of AD by administering a polynucleobase antisense oligonucleotide of U1 snRNP (small nuclear ribonucleoprotein 70 kDa (U1) to a subject in need thereof. In certain embodiments, the antisense oligonucleotide is administered intracranial administration, e.g., by convection enhanced delivery.

In certain embodiments, the disclosure relates to recombinant U1-70K or fragment thereof with or without a LC1 domain optionally conjugated to a detectable marker.

DETAILED DISCUSSION

Figure 1:
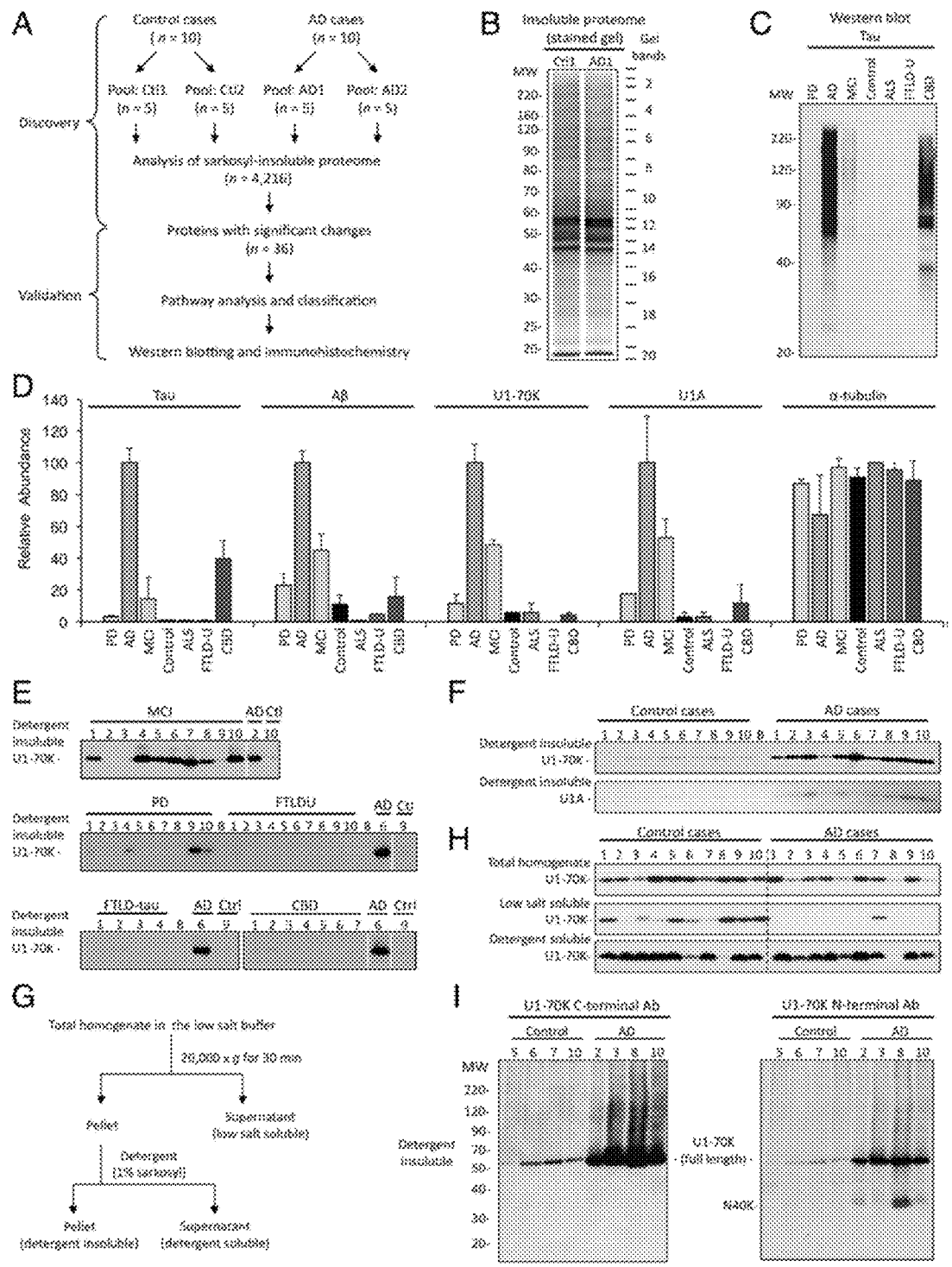
FIG. 1 shows data of proteomic comparisons indicating that U1-70K and U1A are enriched in the sarkosyl-insoluble proteome of AD. (A) Scheme for profiling the aggregated proteins in AD postmortem brains, with non-demented cases as controls (Ctl). (B) A stained SDS gel showing detergent-insoluble proteins in one set of pooled control and AD cases. (C) Similar proteomics analysis of seven groups of neurodegenerative disease samples. One set of sarkosyl-insoluble fractions was immunoblotted by phosphorylated tau antibodies to confirm tauopathies. (D) Relative level of representative sarkosyl-insoluble proteins across different diseases. The level was estimated by spectral counts of these identified proteins, and normalized to set the maximum to 100. Two replicates were analyzed and the bars indicate the values of mean±standard error of the mean (SEM). (E-I) Western blotting analysis of U1-70K or U1A in biochemical brain extracts from control and neurodegenerative cases, and the strategy for protein sequential extraction. The case numbers are shown. B: blank. The exposure time was longer in panel I (left) than in others. At least one AD sample and one control sample were loaded on every gel for comparison.
Figure 2:
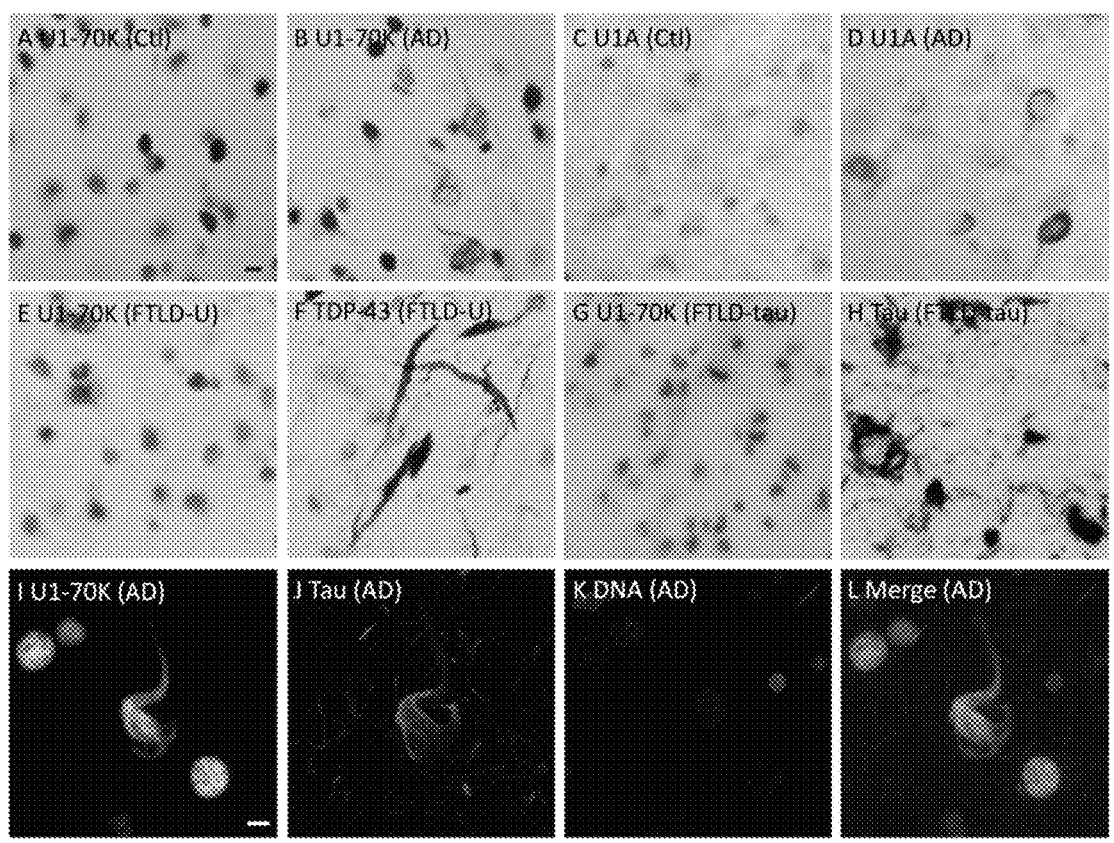
FIG. 2 shows data U1-70K and U1A show neurofibrillary tangles in AD pathology. (A-D) Representative immunohistochemistry images with diaminobenzidine staining of selected control and AD brain slides (50 μm sections, 5 μm scale bar). (E-H) Representative adjacent sections of FTD-U and FTLD-tau cases demonstrating normal U1-70K distribution despite the presence of TDP-43 and tau pathology, respectively. (I-L) Double immunofluorescence staining indicates partial colocalization of U1-70K with tau in AD (5 μm scale bar).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, immunology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" refers any animal, preferably a human patient, livestock, rodent, monkey or domestic pet.

The term "sample" as used herein refers to any biological or chemical mixture for use in the method of the disclosure. The sample can be a biological sample. The biological samples are generally derived from a patient, preferably as a bodily fluid (such as tumor tissue, lymph node, sputum, blood, bone marrow, cerebrospinal fluid, phlegm, saliva, or urine) or cell lysate. The cell lysate can be prepared from a tissue sample (e.g. a tissue sample obtained by biopsy), for example, a tissue sample (e.g. a tissue sample obtained by biopsy), blood, cerebrospinal fluid, phlegm, saliva, urine, or the sample can be cell lysate. In preferred examples, the sample is one or more of CSF, blood, blood plasma, serum, cells, a cellular extract, a cellular aspirate, tissues, a tissue sample, or a tissue biopsy.

The term "polynucleobase" as used herein refers to a polymer comprising bases that bind to naturally occurring nucleic acids bases through base pairing. Nucleic acids may be single or double stranded or both, e.g., they may contain overhangs. Polynucleobases may contain naturally occurring or synthetically modified bases and backbones. In certain embodiments, the nucleobase polymer comprises monomers of phosphodiester, phosphorothioate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, or morpholin-2-ylmethanol, and combinations thereof. In certain embodiments, the nucleobase polymer comprises 5, 10, 15, 20, 30, 40, 50, 60, 70, 80, 90 or more nucleobases. In certain embodiments, the nucleobase polymer comprises 5, 10, 15, 20, 30, 40, 50, 60, 70, 80, 90 or more continuous nucleobases that hybridize to a target sequence. In certain embodiments, the nucleobase probe need not be continuous and may contain one or more insertions, deletions, or hairpins provided that there is sufficient selective binding for identification under typical assay conditions.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

The term "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

U1 Small Nuclear Ribonucleoprotein Complex and RNA Splicing Alterations in Alzheimer Disease (AD)

Proteins were identified that accumulate in Alzheimer's disease or mild cognitive impairment. Unexpectedly, U1-70K and other U1 small nuclear ribonucleoprotein (U1 snRNP) spliceosome components were among them. Multiple U1 snRNP components form cytoplasmic tangle-like structures in AD but not in other examined neurodegenerative disorders, including PD, ALS, and FTLD. Chronic traumatic encephalopathy also shows tangle-like structures with multiple U1 snRNP components. Comparison of brain RNA from AD and control brains reveals dysregulated splicing with accumulation of unspliced RNA species in AD including BIN1, CLU, and PSEN1. In cell culture, U1-70K knockdown or chemical inhibition of splicing increases the protein level of amyloid precursor protein. Thus, these results indicate a U1 snRNP pathology and implicate abnormal RNA splicing in AD pathogenesis.

The RNA-binding protein U1-70K and other U1-specific small nuclear ribonucleoproteins (snRNPs) are sarkosyl-insoluble and associate with cytoplasmic tau neurofibrillary tangles (NFTs) selectively in Alzheimer's disease (AD). The mechanisms underlying the conversion of highly soluble nuclear U1 snRNPs into insoluble cytoplasmic aggregates was studied. Immunogold electron microscopy was used to demonstrate that U1-70K associates with filamentous structures that resembled twisted-ribbon NFTs. Nearly all U1-70K was sarkosyl-insoluble in AD brain tissue, but not in control brain tissue, following biochemical fractionation despite the majority of U1-70K displaying normal nuclear subcellular localization by immunohistochemistry in AD cortical sections. AD brain homogenate could induce endogenous soluble U1-70K from control brain homogenate or recombinant U1-70K to aggregate and become sarkosyl-insoluble indicating that biomolecules harbored within AD brain seed or sequester normal U1-70K. This phenomenon is independent of RNA, does not correlate with phosphorylated tau levels, and requires the presence of sarkosyl-insoluble proteins in AD including U1-70K. Finally, by expressing recombinant N- and C-terminal truncations of U1-70K it was determined that the highly disordered low complexity C-terminus is necessary for U1-70K seeding.

AD brain homogenate containing insoluble U1-70K aggregates and with a variable burden of classical neurofibrillary tangles (i.e., paired helical filaments), can induce the aggregation of endogenous soluble U1-70K from control brain homogenate or recombinant U1-70K and render it sarkosyl-insoluble. The mechanisms that underlie this phenomenon appear to be RNA independent and are associated the presence of the sarkosyl-insoluble protein fraction of AD including U1-70K. Interestingly, a correlation between pTau expression levels and the extent of U1-70K seeding ability was not shown. By expressing both N- and C-terminally truncated fragments of rU1-70K it was determined that any protein construct containing the LC1 domain (amino acids 231-308) was sufficient for seeding by the AD homogenate. Similar LC domains found in a variety of RNA binding proteins including the ALS associated FUS, TDP-43 and hnRNPA1, form amyloid-like fibers in disease and have been shown to aggregate in a (template-directed) prion-like manner in neurodegenerative disease (19, 37, 38). Taken together our data provides preliminary support for a similar aggregation mechanism for U1-70K in AD brain.

In certain embodiments, this disclosure contemplate methods of treating or preventing AD by administering an effective amount of a compound that binds the LC1 domain (amino acids 231-308) to a subject in need thereof. In certain embodiments, the compound is an antibody that binds to the LC1 domain. In certain embodiments, the subject is a human subject.

A b-isox compound can be used to precipitate and identify hundreds of RNA splicing factors with LC domains from either cell and tissue extracts. Kato et al., Cell-free formation of RNA granules: low complexity sequence domains form dynamic fibers within hydrogels, Cell 149, 753-767 (2012). Several of the identified RNA binding proteins were shown to undergo concentration-dependent aggregation and phase transition to a hydrogel-like state composed of uniformly polymerized amyloid-like fibers in vitro. Subsequent investigation identified the LC domains as associated with aggregation and subsequent polymerization. After adopting an aggregated conformation, these proteins can trap and convert native conformers in a template-directed polymerization mechanism. In a process termed heterotypic seeding, these LC-domains are capable of seeding multiple distinct proteins containing LC domains of similar, but not necessarily identical sequences. However, unlike the formation of pathogenic protein fibrils, hydrogel formation is thought to be dynamic and reversible. These results were proposed as a mechanism for understanding how higher-order cellular structures such as RNA granules, comprised entirely of proteins and RNA, assemble in the absence of lipid membranes. To this end, the spliceosome is also a higher-order cellular structure comprised entirely of RNA and proteins—almost all which have intrinsically disordered low complexity sequences. Therefore, it is possible that the mechanisms underlying spliceosome assembly could parallel those of RNA granule assembly. In support of this hypothesis the entire U1 snRNP complex and many spliceosome associated SR-rich splicing factors were recently precipitated from nuclear extracts using the b-isox compound. Thus, it is possible that in human AD brain, the observed U1-70K aggregates have adopted an aberrant hydrogel-like configuration fibrils comprised of U1-70K and possibly other U1 snRNP members, including Sm ring proteins and U1-A, which also contain LC domains. The observation by electron microscopy that U1-70K associates with cytoplasmic PHF ultrastructure is remarkable given that U1-70K is efficiently shuttled to the nucleus and incorporated into U1 spliceosomes in cells such that the concentration of any U1 component protein and particularly of U1 snRNP would be far too low to support hydrogel formation. This indicates an intriguing possibility that in the cytoplasm of cells in AD brain, conditions prevail which locally enhance U1 snRNP protein concentrations, perhaps by a scaffolding mechanism. It is possible that: 1) amyloid oligomers or Tau fibrils could play a role in such a mechanism, 2) U1 snRNP protein aggregates are hetero- or homotypic, and 3) amyloid production or tau fibrillization are possibly occurring as a functional consequence of either a gain or loss of U1 snRNP function.

Figure 7:
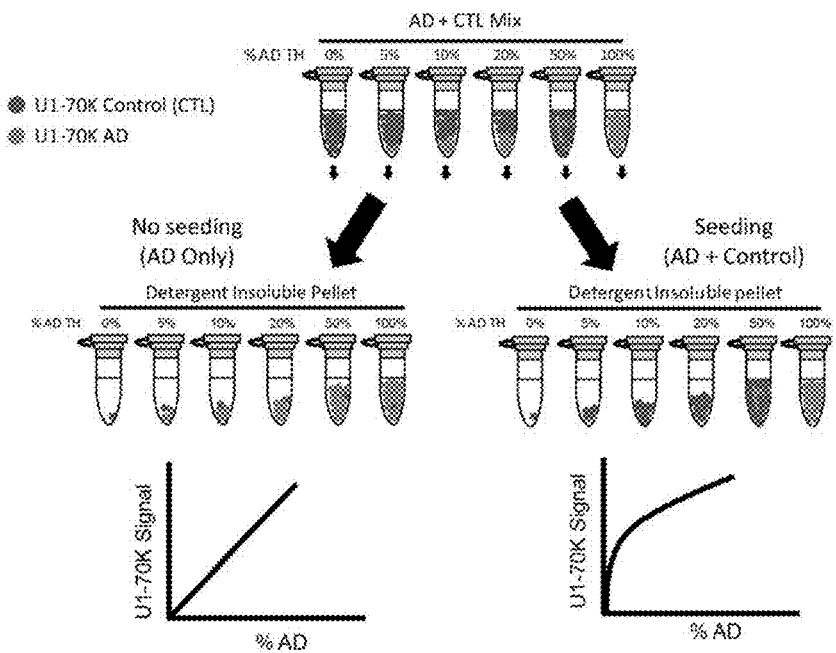
FIG. 7 shows data indicating AD homogenates can seed normal soluble U1-70K from control human brain. (A) AD and control homogenates were mixed in six ratios with an increasing percent AD homogenate, incubated 4 hrs at 4° C. and fractionated into detergent-soluble and detergent-insoluble fractions. If no seeding effect were observed, there should exist a linear relationship between increasing percent AD homogenate and increasing signal of sarkosyl-insoluble U1-70K (A, left panel). If a seeding effect were observed, quantitative western blotting should reveal a non-linear relationship between increasing percent AD homogenate and increasing signal of sarkosyl-insoluble U1-70K, indicative of sequestration of soluble U1-70K from control brain into the detergent-insoluble fraction (A, right panel). (B) Sarkosyl-insoluble fractions of control-AD homogenates mixed in six ratios of increasing percent AD homogenate were western blotted (WB) for U1-70K. Western blotting of the insoluble fractions of control-AD mixtures (AD+Control) revealed a non-linear increase in the signal of sarkosyl-insoluble U1-70K, consistent with the sequestration of soluble control U1-70K into the insoluble fraction. In contrast, insoluble fractions of matching quantities of AD homogenates alone (AD alone) revealed a linear relationship between the amount of brain homogenate and the resulting U1-70K signal. No difference in global levels of U1-70K from AD or control homogenates was observed. TDP-43 was used as a loading control across the AD and control mixtures. (C) Densitometry analysis of three biological replicates indicates significant enrichment of U1-70K in AD-Control mixtures compared to AD alone. Statistical significance (*) was calculated using Student's t-test ($p<0.05$).
Figure 7:
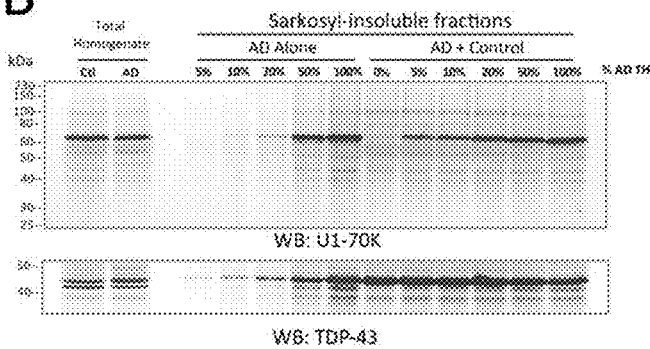
Figure 7:
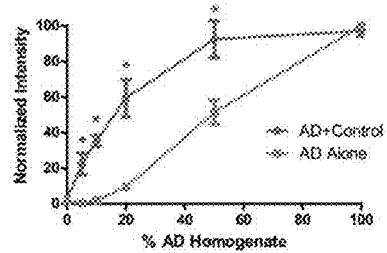

The ability of U1-70K or other aggregated U1 snRNP-proteins to indiscriminately cross-seed (i.e., by heterotypic seeding) other proteins is unlikely, as TDP-43 was not found to be sequestered by AD brain homogenate: In seeding experiments with control and AD brain homogenates, the signal of sarkosyl-insoluble TDP-43 did not increase with increasing amount AD homogenate and remained constant despite increasing amount of AD homogenate. (FIG. 7). Similarly, despite both proteins harboring LC domains, U1-70K does not aggregate in FTLD cases with TDP-43 pathology.

Collectively, these data indicate that U1-70K and TDP-43 likely do not co-aggregate in disease, which may be due to differences in the amino acid composition of their respective LC domains. Alternatively, the hypothesis that local concentration of U1 snRNPs is boosted in distinct cytoplasmic locales by a scaffolding mechanism specific to U1 and not TDP-43 would obviate the apparent contradictions of findings herein with the observations of the McKnight group, wherein they demonstrated that RNA-binding proteins with low complexity domains do seed heterotypically when an appropriately indiscriminant scaffold is provided (i.e., b-isox).

A majority of known yeast prion proteins harbor unique 'prion domains' enriched in glutamine/asparagine (Q/N-rich) and to a lesser degree tyrosine and glycine. These domains are usually at least 60 amino acids in length and are predicted to be intrinsically disordered. Of the 210 RNA recognition motif (RRM)-bearing proteins in the human genome, 29 have a putative prion-like Q/N-rich domain. Nearly half of these 29 proteins were identified among the 106 core b-isox precipitated proteins prepared from cell and tissue extracts. Included in this list were the RNA-binding proteins TAF15, TDP-43, FUS, and hnRNPA1, all of which aggregate in neurodegenerative disease. In contrast, the 78 amino acid LC1 domain in U1-70K, which we have shown is sufficient for aggregation (amino acids 231-308) is comprised almost exclusively of five amino acids (R, E, S, D and K). Of these five, four are organized in highly repetitive tandem arrays of a basic amino acid (R/K) followed by an acidic amino acid (D/E). This domain does not conform to the canonical Q/N-rich LC sequences observed in yeast prion proteins or the prion-like domains of other RNA binding proteins that aggregate in neurodegenerative disease.

U1-70K aggregates are not observed in other tauopathies including CBD and familial forms of FTLD with tau mutations. Moreover, in brain homogenates U1-70K aggregation does not correlate with in sarkosyl-insoluble tau levels. Thus, it is unlikely that U1-70K sarkosyl-insolubility and aggregation in AD brain is due to non-specific interactions with Tau.

Devices for Detection

In certain embodiments, methods of identifying U1 small nuclear ribonucleoproteins or fragments thereof, and associated molecules, which are capable of forming cytoplasmic tangle-like structures utilizing an analytical platform. In certain embodiments, the disclosure contemplates a solid surface array comprising probes to U1 small nuclear ribonucleoproteins or fragments thereof, and associated molecules disclosed herein for the purpose of detecting U1 small nuclear ribonucleoproteins or fragments thereof, and associated molecules.

Probes may be antibodies, fragments, antibody mimetics, or polynucleobases for detection of one or more of the biomarkers. In certain embodiments, the disclosure relates to devices for detection of U1 small nuclear ribonucleoproteins or fragments thereof, and associated molecules, with surfaces comprising attached thereto, at least one reagent specific for each protein in a set of proteins or polynucleobase probes, wherein said set comprises U1 small nuclear ribonucleoprotein is human U1-70K (U1 small nuclear ribonucleoprotein 70 kDa), 40 kD N-terminal fragment of U1-70K, or U1 small nuclear ribonucleoprotein A (U1A), U5 small nuclear ribonucleoprotein 200 kDa helicase, U4/U6.U5 small nuclear ribonucleoprotein 27 kDa protein, U5 small nuclear ribonucleoprotein 40 kDa protein, small nuclear ribonucleoprotein-associated proteins B and B' isoform B, U1 small nuclear ribonucleoprotein C, small nuclear ribonucleoprotein Sm D1, small nuclear ribonucleoprotein Sm D2 isoform 1, small nuclear ribonucleoprotein Sm D3, small nuclear ribonucleoprotein E, small nuclear ribonucleoprotein F, small nuclear ribonucleoprotein G, small nuclear ribonucleoprotein N, splicing factor U2AF 35 kDa subunit isoform a, splicing factor U2AF 65 kDa subunit isoform b, U2 snRNP-associated SURP motif-containing protein, putative RNA-binding protein Luc7-like 2 isoform 1, luc7-like protein 3, probable ATP-dependent RNA helicase DDX46, probable ATP-dependent RNA helicase DDX5, protein LSM2, protein LSM3, protein LSM4, protein LSM5, protein LS6, protein LSM7, splicing factor 3A subunit 1 isoform 1, splicing factor 3A subunit 3, splicing factor 3B subunit 1 isoform 1, pre-mRNA branch site protein p14, splicing factor 3B subunit 3, poly(U)-binding-splicing factor PUF60, probable ATP-dependent RNA helicase DDX23, U1 snRNA, U2 snRNA, U5 snRNA, U4/U6, snRNA, U6 snRNA, serine/arginine repetitive matrix protein 1, serine/arginine repetitive matrix protein 2, serine/arginine-rich splicing factor 1 isoform 1, serine/arginine-rich splicing factor 10 isoform 1, serine/arginine-rich splicing factor 11 isoform 1, serine/arginine-rich splicing factor 12, serine/arginine-rich splicing factor 2, serine/arginine-rich splicing factor 3, serine/arginine-rich splicing factor 4, serine/arginine-rich splicing factor 6; and at least one, two or three reagents specific for a biomarker that measures sample characteristics.

In further examples, provided herein are surfaces wherein said reagent specific for said protein is an antibody, antibody mimetic, or fragment thereof, that is specific for said protein or nucleic acid probe. Provided herein are combinations, comprising the surfaces as described herein having attached thereto at least one reagent specific for a protein or nucleic acid probe and a sample from an individual.

One contemplated test setup is an immune assay, a radioimmunoassay, or a ligand binding assay, e.g., enzyme-linked immunosorbent assay. The protein in the sample is immobilized on a solid support such as a polystyrene microtiter plate either non-specifically by adsorption to spots or zones on the surface or specifically by capture by a probe or ligand—molecule that has affinity for the protein, e.g., antibody specific to the protein. After the protein is immobilized presence is detected. In one example, a detection antibody (e.g., second antibody) is mixed with the surface. If the protein is in the spot, the detection antibody may form a complex with the protein. The detection antibody may be covalently linked to an enzyme that creates a signal upon exposure to appropriate conditions, e.g., by adding an enzymatic substrate to produce a visible signal which indicates the quantity of antigen in the sample. The detection antibody may be itself detected or monitored by a variety of techniques, such as through an antibody with affinity for the detection antibody conjugated to an enzyme. Typically the surface is washed to remove any proteins or antibodies that are not specifically bound.

In certain embodiments, the protein can be immobilized on the surface by ligand binding and a detection reagent will bind specifically to the protein. The detection reagent may be conjugated to an enzyme to generate a signal that can be quantified. For example, Rica & Stevens report an enzyme label that controls the growth of gold nanoparticles and generates colored solutions with distinct tonality when the analyte is present. See Nature Nanotechnology, 2012, 7:821-824.

In certain embodiments, the protein is captured with a ligand or antibody on a surface and the protein is labeled with an enzyme. In one example, a detection antibody conjugated to biotin or streptavidin—to create a biotin-streptavidin linkage to on an enzyme that contains biotin or streptavidin. A signal is generated by the conversion of the enzyme substrate into a colored molecule and the intensity of the color of the solution is quantified by measuring the absorbance with a light sensor. Contemplated assays may utilize chromogenic reporters and substrates that produce some kind of observable color change to indicate the presence of the protein.

In certain embodiments, probes that are fluorogenic, electrochemiluminescent, and real-time PCR reporters are also contemplated to create quantifiable signals. For example, in the case of a polynucleobase, the ends of a string of nucleobases/nucleotides in form of a hairpin may have a FRET-donor or acceptor in close proximity, e.g., at the 3' and 5' ends. The close proximity in the hairpin quenches a signal. However, upon binding to a target sequence the hairpin unfolds separating the donor and acceptor providing a signal. See e.g., Okamoto, Chem. Soc. Rev., 2011, 40: 5815-5828 and Periasamy, Journal of Biomedical Optics 6 (3): 287-291.

Flow cytometry is a laser based technique that may be employed in counting, sorting, and detecting protein by suspending particles in a stream of fluid and passing them by an electronic detection apparatus. A flow cytometer has the ability to discriminate different particles on the basis of color. Particles with different dyes, emitting in two or more different wavelengths, allows the particle to be distinguished. Multiplexed analysis allows one to perform multiple discrete assays in a single tube with the same sample at the same time.

In one example, this surface may be beads each with distinctive combinations of fluorophores that confer each bead a specified, unique color code. Beads act as a solid surface that is coated with capture antibodies of interest. Using the aliquots of the blood sample obtained, sandwich ELISA assay is then performed to detect proteins using reporter-conjugate. Ideally, this assay should be performed in duplicates, to ensure proteins identified are reproducibly found. The beads are passed through a flow cell, on a laser instrument that utilizes two-laser system, in which one laser detects the color code of each bead, and the second laser detects the reporter signal, hence protein concentration. Measured values are statistically analyzed to determine if an alteration in levels is associated with the clinical diagnosis. See Jager et al., Clin Vaccine Immunol, 2003, 10 (1) 133-139.

In certain embodiments, the particles may be polystyrene microspheres that bear carboxylate functional groups on the surface. The particles can be covalently coupled to amine-containing ligands or antibodies to a protein through surface carboxylate groups; alternatively, avidin-coupled particles can be used for binding biotinylated ligands or antibodies. The bound protein can be exposed to fluorescent antibodies or nucleic acid detection reagents to provide a specific signal for each reaction in a multiplexed assay. Each fluorescent detection reagent binds specifically to a protein that is present on only one bead set in a multiplexed assay.

In certain embodiments, the disclosure contemplates individual sets of particles of fluorescently coded particles conjugated with ligands or antibody to proteins. After mixing the particles with a blood sample, the particles are mixed with fluorescent detection antibodies or any fluorescent molecule that will bind to the proteins. Mixtures of particles containing various amounts of fluorescence on their surfaces are analyzed with a flow cytometer. Data acquisition, analysis, and reporting are performed on the particles sets. As each particle is analyzed by the flow cytometer, the particle is classified into its distinct set on the basis fluorescence and values are recorded. As particles are passed through a flow cell, an instrument utilizes two-laser system wherein one laser detects the color code of each particle, and the second laser detects the reporter signal, hence protein concentration.

In certain embodiments, the disclosure contemplates diagnostic methods for measuring or monitoring therapeutic efficacy, In certain embodiments, the disclosure contemplates the seeding phenomonom by which U1 snRNPs from Alzheimer or chronic traumatic encephaolopathy samples, e.g., tissues, biochemically seeds or templates the transformation of soluble snRNP to insoluble snRNP. By mixing homogenates of a test sample, e.g., undiagnosed tissues, with tissue from disease conformations of U1 snRNP, the seeding phenomenon as measured by insolubility transitions would provide confirmation (diagnosis) and measurement of the disease potential of tissues. The insolubility transition could be measured by a variety of means, including gel electrophoresis, column chromatography, antibodies, and other established biophysical and biochemical assays.

There are a number of statistical tests for identifying biomarkers which vary significantly between the subsets, including the conventional t test. However, as the number of biomarkers measured increases, it is generally advantageous to use a more sophisticated technique, such as SAM (see Tusher et al., 2001, Proc. Natl. Acad. Sci. U.S.A. 98(9): 5116-21). Other useful techniques include Tree Harvesting (Hastie et al., Genome Biology 2001, 2:research0003.1-0003.12), Self Organizing Maps (Kohonen, 1982b, Biological Cybernetics 43(1):59-69), Frequent Item Set (Agrawal et al., 1993 "Mining association rules between sets of items in large databases." In Proc. of the ACM SIGMOD Conference on Management of Data, pages 207-216, Washington, D.C., May 1993), Bayesian networks (Gottardo, Statistical analysis of microarray data, A Bayesian approach. Biostatistics (2001), 1, 1, pp 1-37), and the commercially available software packages CART and MARS.

The SAM technique assigns a score to each biomarker on the basis of change in expression relative to the standard deviation of repeated measurements. For biomarkers with scores greater than an adjustable threshold, the algorithm uses permutations of the repeated measurements to estimate the probability that a particular biomarker has been identified by chance (calculated as a "q-value"), or a false positive rate which is used to measure accuracy. The SAM technique can be carried out using publicly available software called Significance Analysis of Microarrays.

A biomarker is considered "identified" as being useful for aiding in the diagnosis, diagnosis, stratification, monitoring, and/or prediction of a disease or condition when it is significantly different between the subsets of biological samples tested. Levels of a biomarker are "significantly different" when the probability that the particular biomarker has been identified by chance is less than a predetermined value. The method of calculating such probability will depend on the exact method utilizes to compare the levels between the subsets (e.g., if SAM is used, the q-value will give the probability of misidentification, and the p value will give the probability if the t test (or similar statistical analysis) is used). As will be understood by those in the art, the predetermined value will vary depending on the number of biomarkers measured per sample and the number of samples utilized. Accordingly, predetermined value may range from as high as 50% to as low as 20, 10, 5, 3, 2, or 1%.

As described herein, the level of at least one biomarker is measured in a biological sample from an individual. The biomarker level(s) may be measured using any available measurement technology that is capable of specifically determining the level of the biomarker in a biological sample. The measurement may be either quantitative or qualitative, so long as the measurement is capable of indicating whether the level of the biomarker in the biological sample is above or below the reference value.

Although some assay formats will allow testing of biological samples without prior processing of the sample, peripheral blood biological fluid samples may be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood. In some examples, the peripheral biological fluid sample is collected in a container comprising EDTA.

The process of comparing a measured value and a reference value can be carried out in any convenient manner appropriate to the type of measured value and reference value for the biomarker at issue. As discussed above, measuring can be performed using quantitative or qualitative measurement techniques, and the mode of comparing a measured value and a reference value can vary depending on the measurement technology employed. For example, when a qualitative calorimetric assay is used to measure biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the disclosure will most commonly be quantitative values (e.g., quantitative measurements of concentration, such as nanograms of biomarker per milliliter of sample, or absolute amount). As with qualitative measurements, the comparison can be made by inspecting the numerical data, by inspecting representations of the data (e.g., inspecting graphical representations such as bar or line graphs).

A measured value is generally considered to be substantially equal to or greater than a reference value if it is at least 95% of the value of the reference value (e.g., a measured value of 1.71 would be considered substantially equal to a reference value of 1.80). A measured value is considered less than a reference value if the measured value is less than 95% of the reference value (e.g., a measured value of 1.7 would be considered less than a reference value of 1.80).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples.

In some embodiments, the methods of the disclosure utilize simple or binary comparison between the measured level(s) and the reference level(s) (e.g., the comparison between a measured level and a reference level determines whether the measured level is higher or lower than the reference level). For protein biomarkers, a comparison showing that the measured value for the biomarker is lower than the reference value indicates or suggests a diagnosis of the disease or condition.

In certain aspects of the disclosure, the comparison is performed to determine the magnitude of the difference between the measured and reference values (e.g., comparing the fold or percentage difference between the measured value and the reference value). A fold difference that is about equal to or greater than the minimum fold difference disclosed herein suggests or indicates a diagnosis of the disease or condition, as appropriate to the particular method being practiced. A fold difference can be determined by measuring the absolute concentration of a protein and comparing that to the absolute value of a reference, or a fold difference can be measured by the relative difference between a reference value and a sample value, where neither value is a measure of absolute concentration, and/or where both values are measured simultaneously. A fold difference may be in the range of 10% to 95%. An ELISA measures the absolute content or concentration of a protein from which a fold change is determined in comparison to the absolute concentration of the same protein in the reference. An antibody array measures the relative concentration from which a fold change is determined. Accordingly, the magnitude of the difference between the measured value and the reference value that suggests or indicates a particular diagnosis will depend on the particular biomarker being measured to produce the measured value and the reference value used (which in turn depends on the method being practiced).

Systems for Measuring Expression

In some embodiments, the determined protein or gene expression, e.g., U1 small nuclear ribonucleoproteins, may be outputted from a visual device. In some embodiments, the outputting may include displaying, printing, storing, and/or transmitting the determined expression. In some embodiments, the determined expression may be transmitted to another system, server and/or storage device for the printing, displaying and/or storing.

The methods of the disclosure are not limited to the steps described herein. The steps may be individually modified or omitted, as well as additional steps may be added.

Unless stated otherwise as apparent from the following discussion, it will be appreciated that terms such as "detecting," "receiving," "quantifying," "mapping," "generating," "registering," "determining," "obtaining," "processing," "computing," "deriving," "estimating," "calculating" "inferring" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

Figure 4:
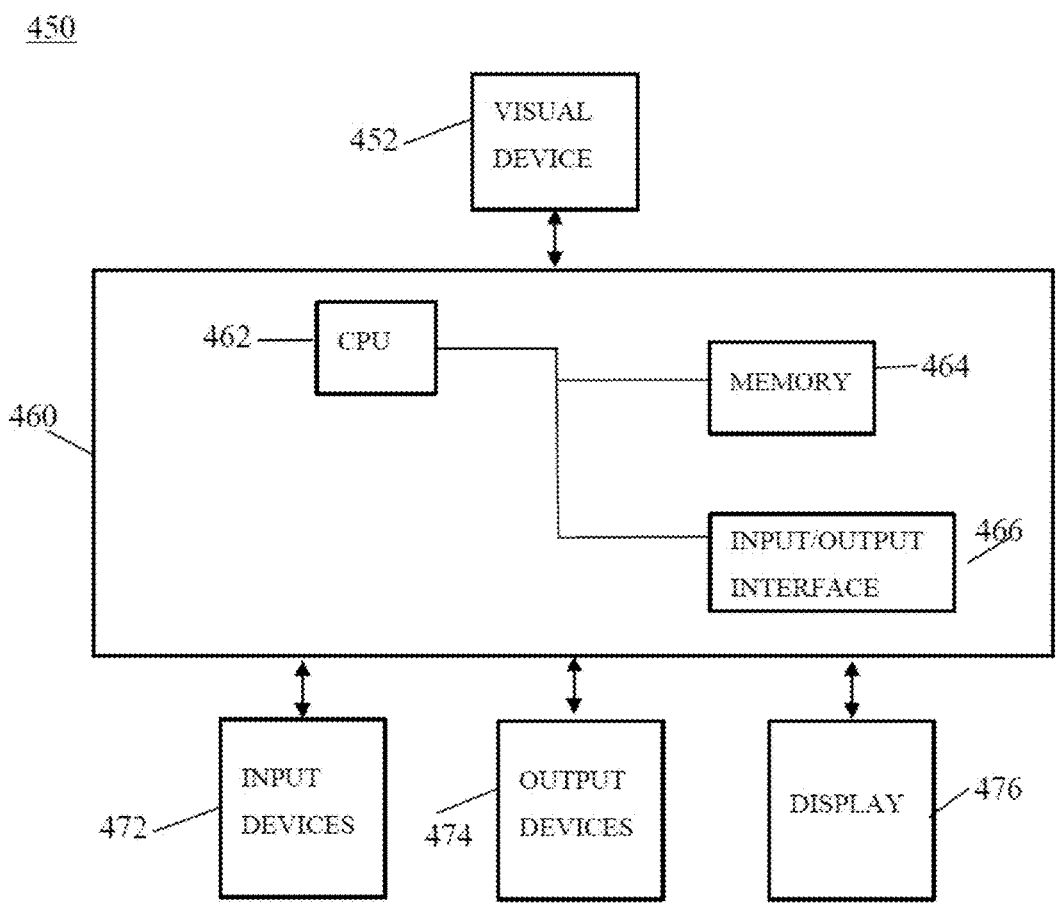
FIG. 4 shows an example of a system configured to determine expression with a visual device.

FIG. 4 shows an example of a system 450 that may be used to quantify expression detected by the sensor according to embodiments. The system 450 may include any number of modules that communicate with other through electrical or data connections. In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the system may be time synchronized. In further embodiments, the system may be time synchronized with other systems, such as those systems that may be on the medical and/or research facility network.

The system 450 may optionally include a visual device 452. The visual device 452 may be any visual device configured to capture changes in a shape, light, or fluorescence. For example, the visual device may include but is not limited to a camera and/or a video recorder. In some embodiments, the visual device may be a part of a microscope system. In certain embodiments, the system 450 may communicate with other visual device(s) and/or data storage device.

In some embodiments, the visual device 452 may include a computer system to carry out the image processing. The computer system may further be used to control the operation of the system or a separate system may be included.

The system 450 may include a computing system 460 capable of quantifying the expression. In some embodiments, the computing system 460 may be a separate device. In other embodiments, the computing system 460 may be a part (e.g., stored on the memory) of other modules, for example, the visual device 452, and controlled by its respective CPUs.

The system 460 may be a computing system, such as a workstation, computer, or the like. The system 460 may include one or more processors (CPU) 462. The processor 462 may be one or more of any central processing units, including but not limited to a processor, or a microprocessor. The processor 462 may be coupled directly or indirectly to one or more computer-readable storage medium (e.g., physical memory) 464. The memory 464 may include one or more memory elements, such random access memory (RAM), read only memory (ROM), disk drive, tape drive, etc., or a combinations thereof. The memory 464 may also include a frame buffer for storing image data arrays. The memory 464 may be encoded or embedded with computer-readable instructions, which, when executed by one or more processors 462 cause the system 460 to carry out various functions.

In some embodiments, the system 460 may include an input/output interface 468 configured for receiving information from one or more input devices 472 (e.g., a keyboard, a mouse, joystick, touch activated screen, etc.) and/or conveying information to one or more output devices 474 (e.g., a printing device, a CD writer, a DVD writer, portable flash memory, display 476 etc.). In addition, various other peripheral devices may be connected to the computer platform such as other I/O (input/output) devices.

In some embodiments, the disclosed methods may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and/or method of the disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures may be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

Antibodies and Antibody Mimetics

In certain embodiments, the disclosure contemplates targeting moieties in any of the epitopes/polypeptides disclosed herein that are antibodies or fragments or chimera, antibody mimetics, or aptamers.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

The modular structure of antibodies makes it possible to remove constant domains in order to reduce size and still retain antigen binding specificity. Engineered antibody fragments allow one to create antibody libraries. A single-chain antibody (scFv) is an antibody fragment where the variable domains of the heavy ($V_H$) and light chains ($V_L$) are combined with a flexible polypeptide linker. The scFv and Fab fragments are both monovalent binders but they can be engineered into multivalent binders to gain avidity effects. One exemplary method of making antibodies and fragments includes screening protein expression libraries, e.g., phage or ribosome display libraries. Phage display is described, for example, in U.S. Pat. No. 5,223,409.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. U.S. Pat. No. 7,064,244.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. No. 7,125,689 and U.S. Pat. No. 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Antibody mimetics or engineered affinity proteins are polypeptide based targeting moieties that can specifically bind to targets but are not specifically derived from antibody $V_H$ and $V_L$ sequences. Typically, a protein motif is recognized to be conserved among a number of proteins. One can artificially create libraries of these polypeptides with amino acid diversity and screen them for binding to targets through phage, yeast, bacterial display systems, cell-free selections, and non-display systems. See Gronwall & Stahl, J Biotechnology, 2009, 140(3-4), 254-269, hereby incorporated by reference in its entirety. Antibody mimetics include affibody molecules, affilins, affitins, anticalins, avimers, darpins, fynomers, kunitz domain peptides, and monobodies.

Affibody molecules are based on a protein domain derived from staphylococcal protein A (SPA). SPA protein domain denoted Z consists of three α-helices forming a bundle structure and binds the Fc protion of human IgG1. A combinatorial library may be created by varying surface exposed residues involved in the native interaction with Fc. Affinity proteins can be isolated from the library by phage display selection technology.

Monobodies, sometimes referred to as adnectins, are antibody mimics based on the scaffold of the fibronectin type III domain (FN3). See Koide et al., Methods Mol. Biol. 2007, 352: 95-109, hereby incorporated by reference in its entirety. FN3 is a 10 kDa, β-sheet domain, that resembles the $V_H$ domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955, hereby incorporated by reference in its entirety.

Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. Anticalins have been generated for targeting the cytotoxic T-lymphocyte antigen-4 (CTLA-4). See Skerra, FEBS J., 275 (2008), pp. 2677-2683, and Binder et al., J Mol Biol., 2010, 400 (4):783-802., both hereby incorporated by reference in their entirety.

The ankyrin repeat (AR) protein is composed repeat domains consisting of a β-turn followed by two α-helices. Natural ankyrin repeat proteins normally consist of four to six repeats. The ankyrin repeats form a basis for darpins (designed ankyrin repeat protein) which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The darpin libraries are typically denoted NxC, where N stands for the N-terminal capping unit, C stands for the C-terminal capping domain and x for the number of library repeat domains, typically between two to four. See Zahnd et al., J. Mol. Biol., 2007, 369:1015-1028, hereby incorporated by reference in its entirety.

Aptamers refer to affinity binding molecules identified from random proteins or nucleic acids libraries. Peptide aptamers have been selected from random loop libraries displayed on TrxA. See Borghouts et al., Expert Opin. Biol. Ther., 2005, 5:783-797, hereby incorporated by reference in its entirety. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. No. 5,475,096, and U.S. Pat. No. 5,270, 163. The SELEX process provides a class of products which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

Antisense Polynucleobase/Oligonucleotide Therapies

In certain embodiments, the disclosure contemplates the treatment or prevention of AD by administering a polynucleobase antisense oligonucleotide of U1 snRNP (small nuclear ribonucleoprotein 70 kDa (U1) to a subject in need thereof. In certain embodiments, the polynucleobase is greater than 10, 15, 18, or 20 continuous nucleotides that hybridize or are the reverse complement of SEQ ID NO: 8

```
GCGGTTCGGC GCGGAAAGCG GGAGGTGGAG GGGCGGCTTG

GGGCAAGCGC GCGCGCGCAG TGCAGAAGCC AGCCCCCCGC

GGCTGAGGTA CTCAAGGTGC CCAAAGGCGG GGTAGTGACC

TCGCGCGTGC GCTGTGCCCG CGGCAGCGCC GGGTCCTAGT

GTGTGGGTTG TTGTTGGCAC CGCACGGCGC GTGCGCAGTG

AGGACGGCGG AGGGATTTGC GGCCGGGACC CACCCCCTGC

TCCAGTCGCT ATCGGAGGCC GCGCGGGTGG CTGAGCAGCG

GCCTGGTGCG CTCGCTTAGC GGGCGACGGA ATCAGACGGA

CGTGGACGCC CCCGGAGTGG AAGCCGAAGC AGGAGTTGTT

GTTGCTGAGG GGCTGCCGCA GCCGCCGCGA GCCTCCGGAC

AGACGCCAGA GCGAGGAGGG CGCTACGCGA CTTGGCAAGA

TGACCCAGTT CCTGCCGCCC AACCTTCTGG CCCTCTTTGC

CCCCCGTGAC CCTATTCCAT ACCTGCCACC CCTGGAGAAA

CTGCCACATG AAAAACACCA CAATCAACCT TATTGTGGCA

TTGCGCCGTA CATTCGAGAG TTTGAGGACC CTCGAGATGC

CCCTCCTCCA ACTCGTGCTG AAACCCGAGA GGAGCGCATG

GAGAGGAAAA GACGGGAAAA GATTGAGCGG CGACAGCAAG

AAGTGGAGAC AGAGCTTAAA ATGTGGGACC CTCACAATGA

TCCCAATGCT CAGGGGATG CCTTCAAGAC TCTCTTCGTG

GCGAGAGTGA ATTATGACAC AACAGAATCC AAGCTCCGGA

GAGAGTTTGA GGTGTACGGA CCTATCAAAA GAATACACAT

GGTCTACAGT AAGCGGTCAG GAAAGCCCCG TGGCTATGCC

TTCATCGAGT ACGAACACGA GCGAGACATG CACTCCGCTT

ACAAACACGC AGATGGCAAG AAGATTGATG GCAGGAGGGT

CCTTGTGGAC GTGGAGAGGG GCCGAACCGT GAAGGGCTGG

AGGCCCCGGC GGCTAGGAGG AGGCCTCGGT GGTACCAGAA

GAGGAGGGGC TGATGTGAAC ATCCGGCATT CAGGCCGCGA

TGACACCTCC CGCTACGATG AGAGGCCCGG CCCCTCCCCG

CTTCCGCACA GGGACCGGGA CCGGGACCGT GAGCGGGAGC

GCAGAGAGCG GAGCCGGGAG CGAGACAAGG AGCGAGAACG

GCGACGCTCC CGCTCCCGGG ACCGGCGGAG GCGCTCACGG

AGTCGCGACA AGGAGGAGCG GAGGCGCTCC AGGGAGCGGA

GCAAGGACAA GGACCGGGAC CGGAAGCGGC GAAGCAGCCG

GAGTCGGGAG CGGGCCCGGC GGGAGCGGGA GCGCAAGGAG

GAGCTGCGTG GCGGCGGTGG CGACATGGCG GAGCCCTCCG
```

-continued

```
AGGCGGGTGA CGCGCCCCCT GATGATGGGC CTCCAGGGGA

GCTCGGGCCT GACGGCCCTG ACGGTCCAGA GGAAAAGGGC

CGGGATCGTG ACCGGGAGCG ACGGCGGAGC CACCGGAGCG

AGCGCGAGCG GCGCCGGGAC CGGGATCGTG ACCGTGACCG

TGACCGCGAG CACAAACGGG GGGAGCGGGG CAGTGAGCGG

GGCAGGGATG AGGCCCGAGG TGGGGCGGT  GGCCAGGACA

ACGGGCTGGA GGGTCTGGGC AACGACAGCC GAGACATGTA

CATGGAGTCT GAGGGCGGCG ACGGCTACCT GGCTCCGGAG

AATGGGTATT TGATGGAGGC TGCGCCGGAG TGAAGAGGTC

GTCCTCTCCA TCTGCTGTGT TTGGACGCGT TCCTGCCCAG

CCCCTTGCTG TCATCCCCTC CCCCAACCTT GGCCACTTGA

GTTTGTCCTC CAAGGGTAGG TGTCTCATTT GTTCTGGCCC

CTTGGATTTA AAAATAAAAT TAATTTCCTG TTGATAGTGG

GC.
```

In certain embodiments, a nucleobase polymer disclosed herein comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl)morpholino) (piperazin-1-yl)phosphinate, or peptide nucleic acids or combinations thereof.

In certain embodiments, a polynucleobase disclosed herein is 3' or 5' terminally conjugated to a hydrocarbon, polyethylene glycol, saccharide, polysaccharide, cell penetrating peptide. Typically, the cells penetrating peptide is a positively charged peptide, arginine-rich peptide, oligoarginine peptide (7-12), or octa-arginine (R8).

In certain embodiments, a polynucleobase disclosed herein comprises 10, 15, 20, 25, 30, 40, 50, 60, 70, 80, 90 or more nucleobases. In certain embodiments, a nucleobase polymer disclosed herein comprises 15, 20, 25, 30, 40, 50, 60, 70, 80, 90 or more continuous nucleobases that hybridize SEQ ID NO: 8.

In certain embodiments, a polynucleobase disclosed herein is the reverse complement of SEQ ID NO: 8 has greater than 80%, 90%, 95% or more sequence identity over a 15, 20, 30, 40, 50, 60, 70, 80, or more nucleobase comparison window.

In certain embodiments, this disclosure relates to pharmaceutical compositions comprising the nucleobase polymer disclosed herein or a particle comprising a nucleobase polymer disclosed herein, and a pharmaceutically acceptable excipient.

EXPERIMENTAL

U1-70K and U1A were Identified from Extraction of Protein Aggregates in AD Subjects Protein aggregates in cortical tissue harvested from 10 AD and 10 age-matched, non-demented cases were analyzed. See FIG. 1A and FIG. 4. Aggregated proteins typically show low solubility and thus were enriched by detergent-based (1% sarkosyl) sequential extraction. The detergent-insoluble samples were then analyzed by gel electrophoresis (FIG. 1B) and liquid chromatography coupled with tandem mass spectrometry. 36 proteins accumulated in AD. The table below shows results of two control case pools (Ctl1 and Ctl2), two AD case pools (AD1 and AD2). The proteins elevated in AD were analyzed by two statistical approaches (false discovery rate <5%). Spectral counts are used as a quantitative index.

TABLE 1

Identified proteins that are accumulated in AD versus control cases[1]

| Accession# | Protein names | Spectral counts[2] | | | |
|---|---|---|---|---|---|
| | | Ctl1 | Ctl2 | AD1 | AD2 |
| Amyloid-beta peptide metabolism | | | | | |
| NP_000475.1 | amyloid beta peptide[3] | 9 | 31 | 169 | 196 |
| NP_000032.1 | apolipoprotein E | 1 | 1 | 49 | 92 |
| NP_115907.2 | collagen, type XXV, alpha 1 isoform 2 | 1 | 0 | 23 | 24 |
| NP_004369.1 | cellular retinoic acid binding protein 1 | 0 | 0 | 9 | 7 |
| Cytoskeleton maintenance | | | | | |
| NP_058519.2 | microtubule-associated protein tau | 10 | 11 | 824 | 989 |
| NP_116757.2 | dystrobrevin alpha | 0 | 11 | 23 | 24 |
| Inflammation | | | | | |
| NP_009224.2 | complement component 4A preproprotein | 7 | 7 | 77 | 128 |
| NP_001002029.3 | complement component 4B preproprotein | 7 | 7 | 81 | 163 |
| NP_000055.2 | complement component 3 | 1 | 2 | 57 | 93 |
| Protein phosphorylation | | | | | |
| NP_005246.2 | cyclin G associated kinase | 0 | 1 | 7 | 11 |
| NP_002842.2 | protein tyrosine phosphatase, zeta1 | 2 | 0 | 9 | 10 |
| NP_644812.1 | T-cell activation protein phosphatase 2C | 0 | 0 | 6 | 7 |
| Synaptic plasticity | | | | | |
| NP_982271.1 | synaptojanin 1 | 17 | 9 | 59 | 56 |
| NP_001626.1 | amphiphysin | 16 | 14 | 44 | 35 |
| NP_640337.3 | syntaxin binding protein 5 | 2 | 9 | 24 | 22 |
| NP_055804.2 | regulating synaptic membrane exocytosis 1 | 0 | 2 | 12 | 11 |

TABLE 1-continued

Identified proteins that are accumulated in AD versus control cases[1]

| Accession# | Protein names | Spectral counts[2] | | | |
| --- | --- | --- | --- | --- | --- |
| | | Ctl1 | Ctl2 | AD1 | AD2 |
| NP_056993.2 | neuroblastoma-amplified protein (with a Sec39 domain) | 0 | 0 | 4 | 10 |
| NP_066973.1 | glutamate receptor interacting protein 1 | 0 | 0 | 7 | 7 |
| *Mitochondrial regulation* | | | | | |
| NP_892022.2 | mitochondrial nicotinamide nucleotide transhydrogenase | 46 | 46 | 133 | 95 |
| NP_066923.3 | mitochondrial NFS1 nitrogen fixation 1 | 11 | 17 | 45 | 40 |
| NP_000134.2 | mitochondrial fumarate hydratase | 5 | 12 | 34 | 33 |
| NP_570847.1 | optic atrophy 1 | 1 | 2 | 15 | 15 |
| NP_004270.2 | mitochondrial processing peptidase | 1 | 1 | 13 | 8 |
| *RNA splicing* | | | | | |
| NP_003080.2 | U1 small nuclear ribonucleoprotein 70 kDa | 2 | 2 | 31 | 39 |
| NP_004587.1 | U1 small nuclear ribonucleoprotein A | 0 | 1 | 12 | 22 |
| NP_055644.2 | ATP-dependent RNA helicase DDX46, Prp5 | 0 | 0 | 9 | 17 |
| *Metabolic reactions* | | | | | |
| NP_001120920.1 | 4-aminobutyrate aminotransferase | 20 | 25 | 56 | 60 |
| NP_036322.2 | 10-formyltetrahydrofolate dehydrogenase | 10 | 16 | 40 | 33 |
| NP_001094346.1 | phytanoyl-CoA dioxygenase domain containing protein 1 | 0 | 0 | 9 | 7 |
| NP_835471.1 | nicotinamide nucleotide adenylyltransferase 3 | 0 | 0 | 7 | 4 |
| NP_149078.1 | asparagine-linked glycosylation 2 | 0 | 0 | 5 | 4 |
| *Others* | | | | | |
| NP_056450.2 | GTPase activating protein and VPS9 domains 1 | 1 | 2 | 13 | 13 |
| NP_065871.2 | phosphatidylinositol-dependent Rac exchanger 1 (P-REX1) | 0 | 0 | 5 | 6 |
| NP_006086.1 | aminophospholipid transporter | 9 | 6 | 24 | 29 |
| NP_055839.3 | RAN binding protein 16 (exportin 7) | 3 | 8 | 24 | 24 |
| NP_055806.2 | ALFY, involved in macroautophagy | 0 | 0 | 5 | 4 |

[1]Results of two control case pools (Ctl1 and Ctl2), two AD case pools (AD1 and AD2). These proteins elevated in AD were analyzed by two statistical approaches (false Discovery rate <5%).
[2]Spectral counts are used as a quantitative index.
[3]RNA splicing factors are microtubule-associated protein tau, U1 small nuclear ribonucleoprotein 70 kDa, U1 small nuclear ribonucleoprotein A, ATP-dependent RNA helicase DDX46, Prp5.

In certain embodiments, the disclosure contemplates methods of diagnosing AD by analyzing protein or protein expression patterns one or more, two or more, three or more, four or more, five or more, ten or more, fifteen or more, or twenty or more of the protein in the above table.

Aβ and tau were abundantly enriched in AD, together with other known proteins regulating Aβ metabolism. Other identified proteins were consistent with the idea that inflammation, phosphorylation networks, synaptic plasticity and mitochondrial regulation are altered in AD. Numerous proteins involved in these pathways are preferentially enriched in the disease tissues. Two subunits (U1-70K and U1A) of the U1 snRNP and the associated RNA helicase Prp519 were highly elevated in the AD insoluble proteome, indicating possible deposition of the U1 snRNP complex.

The same proteomics strategy were used to analyze cases of PD, FTLD-U, ALS, and corticobasal degeneration (CBD), and determined if the U1 snRNP changes are specific to AD or common in other diseases with protein aggregates. Cases of mild cognitive impairment (MCI) were also studied because it is often a prodromal stage of AD and to determine if proteomic changes occur early in the disease. The level of detergent insoluble tau was high in AD and CBD (a prototypical tauopathy), lower in MCI, and barely detectable in PD, FTLD-U, and ALS (FIGS. 1C and 1D); Aβ also showed a marked increase in AD, a moderate increase in MCI, but no accumulation in the other diseases. Importantly, the levels of insoluble U1-70K and U1A were highly correlated with that of Aβ rather than tau, supporting the conclusion that U1 snRNP accumulation is specific to AD and occurs early during the disease development.

To confirm the proteomic changes and further analyze the aggregation of U1 snRNP proteins in individual disease cases, specific antibodies were used to probe for U1-70K and U1A in brain extracts (FIG. 1E, 1F). The detergent insoluble U1-70K was increased in all 10 AD cases as well as in 7 out of 10 MCI cases; U1A accumulated in 8 out of 10 AD cases. In contrast, U1-70K was not aggregated in any other cases of PD, FTLD-U, FTLD-tau, and CBD, except for three PD samples. Re-examination of these three PD cases with additional histochemical staining identified co-existing AD plaque and tangle pathology. These data strongly validate the uniqueness of U1 snRNP accumulation to AD.

The total protein level of U1-70K and to characterize U1-70K biochemically in AD brain was examined. Samples were homogenized and extracted using three buffers with increasing stringency: a low salt buffer, a sarkosyl-containing solution, and 8 M urea (FIG. 1G). In a comparison of AD and control cases (FIG. 1H), U1-70K displayed no obvious difference in either the total homogenate or the sarkosyl soluble fraction. Intriguingly, the low salt extracted U1-70K was decreased in AD cases (~3-fold difference). This result, together with the enrichment of U1-70K in the sarkosyl-insoluble (i.e., urea) samples, indicates that the biophysical characteristics of U1-70K are altered in AD, resulting in its aggregation and depletion from the low salt soluble pool. These findings suggest a possible loss of U1-70K function in AD.

Aggregation of protein proteolytic fragments is common in neurodegeneration. In the AD samples, U1-70K was identified by mass spectrometry in two regions of the SDS gels (~70 kD and ~40 kD, FIG. 1B), and the 40 kD region contained only N-terminal peptides of U1-70K. The heterogeneous N-terminal fragments were confirmed by immunoblotting using antibodies specific to either N-terminus or C-terminus of U1-70K (FIG. 1I). Thus, U1-70K is internally cleaved and the resulting N-terminal fragments are detected in the detergent insoluble proteome. Structural analysis20 indicates that the first 100 residue region in U1-70K is intrinsically disordered and may contribute to the aggregation process.

U1-70K and Tau Deposition in AD

Immunohistochemical analysis was performed to examine the localization and accumulation of U1 snRNP protein components in AD. These studies revealed that U1-70K and U1A form cytoplasmic tangle-like aggregates in 17/20 and 9/10 AD cases, respectively, but not in controls (FIG. 2A to 2D). These pathological changes were not present in FTLD-U and FTLD-tau cases (2E to 2H) despite the presence of TDP-43 (2F) and tau (2H) pathology. PD and CBD cases also did not show abnormal accumulations of U1 snRNP protein components. Other RNA splicing factors like heterogeneous nuclear ribonucleoprotein A/B (hnRNP A/B), recently suggested as a dysfunctional splicing factor in AD, and serine/arginine repetitive matrix protein 2 (SRRM2) did not demonstrate tangle-like aggregates suggesting that this may be a U1 snRNP specific process. Although pure tauopathies (e.g. FTLD-tau and CBD) do not show U1-70K aggregation, double staining of AD cases indicates that U1-70K inclusions are closely associated with tau-immunoreactive neurofibrillary tangles (FIGS. 2I to 2L), implying possible relationship between the mechanisms of U1-70K and tau deposition in AD. These data indicate specific U1 snRNP pathology in AD.

The specific association of U1 snRNP pathology with AD and the strong correlation between U1-70K and Aβ abundance in the insoluble AD proteome prompted investigation if Aβ accumulation itself can induce U1-70K pathology using an AD mouse model (APP/PSEN1 double transgenic mice). Even in old animals (i.e. 23-month-old) with robust plaque staining, no U1-70K pathology was detected. It was concluded that U1 snRNP pathology is uniquely associated with human AD. The pathological findings are not replicated in a mouse model of amyloidogenesis suggesting that U1 snRNP abnormalities are not a direct consequence of Aβ production or deposition.

Loss of Nuclear Spliceosome Function

The biochemical and pathological changes in U1 snRNP components in AD brains suggests a possible loss of nuclear spliceosome function. To address this possibility, deep RNA sequencing of frontal cortex RNAs was performed using two independent sample groups from the brain banks of Emory University (4 control and 5 AD cases) and the University of Kentucky (UKY, 3 control and 3 AD cases). In both groups, a higher proportion of AD brain-derived reads mapped to intronic sequences of known genes (p=0.027 in Emory cases, p=0.010 in UKY cases; FIG. 3A). For individual genes, the ratio between length-normalized intronic and exonic reads were defined as a splicing deficiency score. The distribution of the splicing deficiency scores of all mapped genes indicated splicing defects in AD (n=15,934 in Emory cases, n=20,366 in UKY cases; $p<1\times10^{-15}$ in both groups; FIG. 3B). A large percentage of genes were found to be affected in AD (74% in Emory cases, 76% in UKY cases; 20% false discovery rate; FIG. 3B). To confirm these findings, a NanoString approach was applied to analyze 12 selected transcripts implicated in AD pathogenesis using high quality RNA samples (average RNA integrity number score=8.0; 14 control and 15 AD cases). For each gene the ratio between pre-mRNAs (i.e. exon1-intron1) and mature mRNAs (i.e. exon1-exon2) was quantified as a measure of splicing efficiency. The splicing efficiency for 8 (75%) transcripts in the AD cases showed significant reduction (i.e. an increase in exon1-intron1 RNAs; p<0.05; FIG. 3C). Finally, using traditional quantitative RT-PCR methods, the results were validated for 3 transcripts (BIN1, CLU, and PSEN1). Taken together, these results indicate a global alteration in RNA maturation in AD.

To assess U1 snRNP loss of function in an experimental system, U1-70K knockdown was performed in HEK293 cells in order to determine possible effects on APP metabolism. Indeed, U1-70K knockdown (<10% remaining) induced an increase in endogenous APP and Aβ40 when compared to the scrambled siRNA control. Chemical inhibition of splicing by isoginkgetin also led to striking accumulation of APP in both HEK293 cells and SK-N-SH neuroblastoma cells. Human APP has three isoforms (APP770, APP751 and APP695) generated by alternative splicing. RT-PCR analysis indicated that U1-70K knockdown or isoginkgetin inhibition resulted in a decrease of APP770 transcript and an increase of APP751 and APP695 transcripts. This upregulation of APP was also observed in differentiated SH-SY5Y neuroblastoma cells and in human embryonic stem cell derived neurons. While an isoform-switching phenomenon in human brain was not observe, NanoString experiments found an increase in RNA species containing contiguous exon1-intron1 sequences for APP in AD (p=0.068; FIG. 3C). These results indicate that disruption of RNA splicing function may result in mechanistically relevant changes in APP expression.

In addition to a role in splicing, U1 snRNP is recruited to nascent transcripts to suppress premature cleavage and polyadenylation (PCPA) on cryptic poly(A) sites, and moderate inhibition of U1 snRNP by antisense morpholino oligonucleotide (AMO) leads to PCPA in a 5'-3' direction. Examination of RNA sequencing (RNA-seq) data revealed more poly(A)-containing reads in the 5' end of transcripts among AD cases than controls in both Emory and UKY groups (n=13,315 in Emory group, n=11,431 in UKY group; $P<1\times10^{14}$) in both groups; FIG. 3D). These data suggest the intriguing possibility that partial loss of U1 snRNP function in AD might result in increased PCPA in addition to altered splicing.

U1 snRNP Deficiency Alters Amyloid Precursor Protein (APP) Expression and Aβ Levels.

Figure 3:
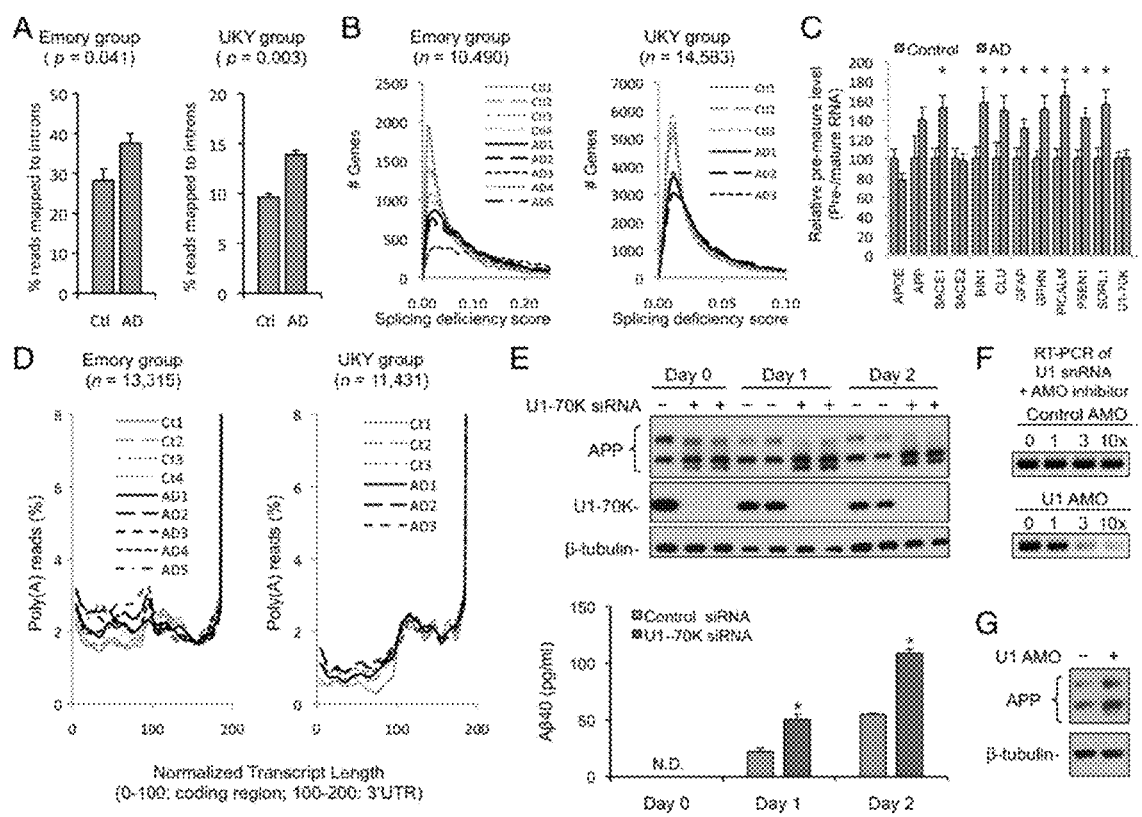
FIG. 3 shows data indicating RNA splicing impairment in AD, and up-regulation of APP and Aβ upon splicing inhibition. (A) The frequency of summed intron reads is higher in AD than in control. The bars indicate mean±SEM (P value derived by Student t test). The Emory and UKY samples were processed independently. The batch discrepancy may be due to sample quality difference and experimental variations. (B) The histograms of splicing deficiency scores of all mapped genes show a statistically significant difference between AD and control in both Emory and UKY groups ($P<2.2\times10^{-16}$ for both groups, Kolmogorov-Smirnov test). (C) Evaluation of RNA splicing efficiency by measuring mRNAs and pre-mRNAs of selected genes in control and AD cases. The bars indicate the values of mean±SEM (AD: n=15; control: n=14; asterisks: $P<0.05$, Student t test). (D) Poly(A)-containing reads from 5' to 3' of every gene were defined and normalized according to the total poly(A) reads of the gene. Every transcript was divided into coding region (0-100, from start to stop codon) and 3' UTR region (100-200), then into 20 bins. The poly(A) read percentage in each bin was averaged for all genes in every case, and plotted to represent the frequency of PCPA. The PCPA frequency was markedly different between control and AD cases ($P<2.2\times10^{-16}$ for Emory group, $P<6.9\times10^{-15}$ for UKY group, Kolmogorov-Smirnov test). (E) U1-70K knockdown increases APP and Aβ40 levels in HEK293 cells. The cells were transfected for 2 d, then cultured in a low-serum medium and harvested at day 0, 1, and 2 for analysis (asterisks: $P<0.05$, Student t test; N.D., not detected). APP and Aβ40 were analyzed by immunoblotting and ELISA, respectively. (F) PCR to examine the specificity of U1 AMO. The reaction was designed to amplify the U1 RNA 5'-end region with the addition of control AMO or U1 AMO as inhibitory competitor. (G) The APP level increases upon AMO inhibition of U1 snRNP.

To assess U1 snRNP loss of function in an experimental system, U1-70K knockdown in HEK293 cells was performed. Possible effects on APP metabolism were determined. U1-70K knockdown (<10% remaining) induced an increase in endogenous APP and Aβ40 compared with the scrambled siRNA control (FIG. 3E). Human APP has three isoforms (APP770, APP751, and APP695) generated by alternative splicing. RT-PCR analysis indicated that U1-70K knockdown in a decrease of APP770 transcript and an increase of APP751 and APP695 transcripts. This up-regulation of APP and Aβ40 was also observed in differentiated SH-SY5Y neuroblastoma cells. In addition to U1-70K knockdown, U1 AMO inhibition of U1 snRNP function elevated APP level as well (FIGS. 3 F and G). Though we did not observe an obvious isoform-switching phenomenon in human brain, NanoString experiments found an increase in RNA species containing contiguousexon1-intron1 sequences for APP in AD (P=0.068; FIG. 3C). These results indicate that disruption of RNA splicing function may result in mechanistically relevant changes in APP expression.

Sample Pooling

One major challenge to study human postmortem brains is that the specimens are usually associated with large biological variations (e.g. genetic background, age, and gender), which are further confounded by a wide range of uncontrollable factors, such as environmental elements (e.g. diet, lifestyle), antemortem and pharmacological treatments, end-of-life illnesses, postmortem interval, and tissue storage conditions. To minimize the variations caused by the confounding factors, the following strategies were employed: (i) to use well-characterized brain specimens diagnosed by consensus clinical and neuropathological criteria; (ii) to select brain tissues without large bias in race, age and gender; (iii) to enhance datasets by correlating protein changes with disease progression (e.g. MCI and AD); (iv) to adapt a pooling strategy (FIG. 1A) to average variations induced by the confounding factors.

Although an ideal method is to perform deep proteomics analysis for a large number of tissues independently, it is not practicable with current throughput of proteomics platforms. The main caveat of pooling is that samples of poor quality (e.g. degraded or contaminated) may negatively influence the result of the entire pool. To address this problem, the integrity of brain homogenates were tested prior to pooling. An aliquot of the samples was analyzed by a SDS gel to confirm that global protein patterns were comparable and protein degradation was minimal. Finally, one biological replicate was implemented for each pool to facilitate statistical evaluation of differentially expressed proteins.

Sequential Biochemical Fractionation

The brain tissues were sequentially extracted with a low salt buffer (10 mM Tris, pH 7.5, 5 mM EDTA, 1 mM DTT, 10% sucrose, Sigma protease inhibitor cocktail, ~10 ml buffer per gram tissue), a detergent buffer (the low salt buffer with the addition of 1% sarkosyl, N-Lauroyl-sarcosine), and finally 8 M urea with 2% SDS. See Gozal et al., J. Proteome Res. 8, 5069-5079 (2009) and Gozal et al., Mol. Neurodegener., 6, 82 (2011). Generally, the protein yield in final urea samples (detergent insoluble fractions) during sequential extraction was approximately 2% of the starting material.

Protein Identification by Shotgun Mass Spectrometry

Mass spectrometry analysis of detergent insoluble fractions was processed by LC-MS/MS. Protein concentration was determined by bicinchoninic acid (BCA) assay (Thermo Scientific) using bovine serum albumin as standard, and further verified by Coomassie staining on a short SDS gel. Approximately 50 μg of protein per sample were resolved on a 9% SDS gel and stained with Coomassie blue. Each gel lane was excised into 20 bands followed by in-gel trypsin digestion. The resulting peptides were analyzed by LC-MS/MS (2 h) on an LTQ-Orbitrap mass spectrometer (Thermo). A total of ~640 h MS running time was spent in this project.

MS/MS spectra were searched against a human reference database from the National Center for Biotechnology Information using the SEQUEST Sorcerer algorithm (version 2.0, SAGE-N). Searching parameters included mass tolerance of precursor ions (±20 ppm) and product ion (±0.5 Da), partial tryptic restriction, fixed mass shift for modification of carboxyamidomethylated Cys (+57.0215 Da), dynamic mass shifts for oxidized Met (+15.9949 Da), three maximal modification sites and three maximal missed cleavages. Only b and y ions were considered during the database match. To evaluate false discovery rate during the spectrum-peptide matching, all original protein sequences were reversed to generate a decoy database that was concatenated to the original database. False discovery rate (FDR) was estimated by the number of decoy matches (nd) and total number of assigned matches (nt), according to $$FDR = 2 \times nd/nt$$

assuming mismatches in the original database were the same as in the decoy database. To remove false positive matches, assigned peptides were grouped by charge state and then filtered by minimal peptide length (7 amino acid), mass-to-charge accuracy (±5 ppm) and matching scores (XCorr and deltaCn) to reduce protein FDR below 1%. Furthermore, all proteins identified by a single spectral count were removed, which eliminated all decoy matches. If peptides were shared by multiple members of a protein family, the matched members were clustered into a single group. Based on the principle of parsimony, the group was represented by the protein with the highest number of assigned peptides, and by other proteins if they were matched by unique peptide(s), resulting in the acceptance of 4,216 proteins in two control pools and two AD pools.

Label-Free Protein Quantification and Statistical Inference

To identify differences between the control and AD cases, the proteins in multiple samples based were quantified on spectral counts (SC). The spectral counts were first normalized to ensure that the average SC per protein was the same in all datasets. Two statistical approaches were used: a straightforward G-test analysis and a one-sided z-test analysis.

The G-test was previously used to judge statistical significance of protein abundance difference. Briefly, the G-value of each protein was calculated as shown in the equation below:

$$G = 2 \times (S1 \times \ln [S1 \div ((S1+S2) \div 2)] + S2 \times \ln [S2 \div ((S1+S2) \div 2)])$$

where S1 and S2 are the detected spectral counts of a given protein in any of two samples for comparison, respectively, and "ln" is the natural logarithm. Although theoretical distribution of the G values is complex, these values approximately fit to the $\chi 2$ distribution (one degree of freedom), allowing the calculation of related p values.

A reliable p value threshold was set up to identify protein changes with statistical significance. Ideally, the threshold should accept a very small number of proteins (i.e. false discoveries) in null experiments (e.g. comparison of control 1 versus control 2; or comparison of AD 1 versus AD 2). When the same threshold was used for AD-control comparison, the list is deemed acceptable with a low false discovery rate. To find the appropriate threshold, the p value was dynamically adjusted from 0.4 to 0.001, and p value of 0.04 was identified as a reasonable threshold with balanced sensitivity and specificity (false discovery rate ~5%), resulting in the acceptance of 63 proteins. these proteins were manually examined and protein paralogs were removed, reducing the final list to 43 proteins.

In addition, a z-test analysis was developed to analyze the data in multiple steps. (i) The spectral counts were standardized and square root of spectral counts was used to stabilize the variance within each group (i.e. control or AD). (ii) For each group, a parameter phi was estimated to represent technical variance plus minimal biological variance. This was accomplished by a trimmed average of the sample variances: trimming off the largest 5% and smallest 5% of the sample variances so that the estimated phi was resistant to outliers. (iii) Each protein's variance was estimated using a shrinkage estimator, in which a given protein's variance was based on a weighted average of phi and the protein-specific sample variance in only two observations (i.e. two pools). The weights were calculated using an empirical Bayes approach (w1=0.8 for phi and w2=0.2 for the protein-specific sample variance). (iv) p values were derived under the assumption that z-tests were independent and normally distributed. the original FDR controlling procedure of Benjamini and Hochberg was used to set a threshold corresponding to an estimated FDR of 5%. (v) After manually examination and removal of protein paralogs, a list of 61 proteins were accepted.

Finally, we accepted 36 proteins (Table 1) passing the thresholds of both statistical approaches (less than 5% FDR).

Antibodies

Two polyclonal rabbit U1-70K antibodies were developed and purified using synthetic peptides: GDAFKTLF-VARVNYDTTESKLR (SEQ ID NO: 9, N-terminal amino acid 99-120), and GGDGYLAPENGYLMEAAPE (SEQ ID NO: 10, C-terminal amino acid 419 to 437). Other commercial antibodies include: APP (22C11, Millipore; Y188, Epitomics), tau (ATB, Pierce), U1A (WH0006626M1, Sigma), SmN (HPA003482, Sigma), SmD1 (50940, Abcam), hnRNP A/B (98273, Santa Cruz), SRRM2 (122719, Abcam), actin (6276, Abcam), and NF-H (Sigma).

Immunohistochemical Staining

Fixed, cryopreserved free floating sections (50 μm thick) were incubated with 3% hydrogen peroxide to quench endogenous peroxidase activity, blocked and permeabilized. The sections were incubated sequentially with the primary antibody, biotinylated or fluorescently conjugated secondary antibodies, and then developed by an avidin-biotin-peroxidase complex method (Vector Laboratories) with 3,3'-diaminobenzidine (DAB) or fluorescein isothiocyanate-tyramide amplification (Perkin-Elmer). Paraffin-embedded sections (8 μm thick) were deparaffinized and analyzed using a similar protocol.

RNA Deep Sequencing Data Acquisition

The mRNA-seq was performed according to the Illumina standard kit protocol. Starting samples included human control and AD specimens from the Emory University ADRC brain bank. TRIzol (Invitrogen) extracted RNA was used for polyA RNA purification and converted to cDNA. The double stranded cDNA fragments were ligated to Illumina paired end adaptors, followed by size selection (~200 bp). Finally, the libraries were enriched using PCR and analyzed by HiSeq 2000 sequencing systems (Illumina). The initial RNA quality was evaluated by the values of RNA integrity number (RIN). It was a challenge to obtain RNA samples from port-mortem human brain specimens. We screened over 20 human brain samples from the Emory brain banks and finally selected 5 AD and 4 control cases (RIN 4.4-7.7) for RNA-seq analysis. Approximately 34-52 million reads were acquired for each sample.

To replicate the analysis, samples were obtained with much shorter postmortem interval from the University of Kentucky brain bank. high quality RNA samples (RIN 7.8-8.8) were isolated and deep RNA-seq analysis was performed. Approximately 78-108 million reads were acquired for each sample.

RNA-Seq Sequence Alignment and Analysis

Paired end reads were mapped to UCSC human reference genome hg19 using Illumina iGenomes pre-built indexes and TopHat programs: TopHat (v2.0.3), and Bowtie (2.0.0.5). Default parameters were used except that a GTF file with known transcripts was also provided (-G parameter). This additional file permitted TopHat to map reads in multiple stages. Initially, all reads were mapped to a virtual transcriptome (i.e. a full RefSeq set of 36,047 transcripts). Only if the reads were not fully mapped to the transcriptome, they would be mapped to the genome. Finally, the reads mapped to the transcriptome were converted to genomic mapping, and merged together in the final output BAM files. During the transcriptome-to-genome conversion, the skipped regions of the genome (due to introns) were captured in the CIGAR string of the resulting BAM files.

To extract the reads mapped to whole genes, including exons and introns, the BAM to BED files were converted using bedtools, and used Table Browser program to generate three BED files: (i) RefSeq Genes (Whole Gene), (ii) RefSeq Genes (Exons) and (iii) RefSeq Genes (Introns). Finally, we used intersectBed (v2.16.1) to define the intersections between mapped reads and the three RefSeq BED files.

The global splicing deficiency was first evaluated by the percentage of reads mapped to introns, after normalized to the total reads mapped to whole genes. The two-tailed student t-test analysis was performed to evaluate the p values (FIG. 3A). Moreover, a splicing deficiency (Sd) score was defined for each gene as the ratio of length-corrected read counts aligned to introns and exons:

$$Sd = (\text{\# intronic reads/total intronic length}) \div (\text{\# exonic reads/total exonic length})$$

A high Sd value indicated low splicing efficiency. The histogram of the S value distribution was shown for every case (FIG. 3B). The Kolmogorov-Smirnov test was used to analyze statistical significance of the comparison between AD and control cases. Finally, the method of Significance Analysis of Microarrays (SAM) was used to computer p values and FDR and analyzed the effect of FDR on the acceptance of false positives and false negatives. As the sample size in this RNA-seq study was relatively small, 20% FDR showed a reasonable balance between false positives and false negatives.

In addition, both the percentage intronic reads and the Sd scores between the Emory and UKY groups were different. As the Emory and UKY samples were processed independently, the batch discrepancy may be due to the difference in sample quality and other technical variations, including experimental settings in brain sample collection, RNA purification and RNA-seq data acquisition. Nevertheless, during the comparison of AD and control cases in the same batch, the results were highly consistent and reproducible in two groups of samples.

Amplification-Free Counter Assay and qRT-PCR for Relative Quantitation of Pre- and Mature mRNA Total RNA was extracted from frontal cortices (0.5-1.0 g per sample) using TRIzol (Invitrogen), and assayed by the N-Counter gene expression system (NanoString Technologies, Seattle Wash., 100 ng total RNA per sample, RIN 7.8-8.8) using capture and reporter probes complementary to a 100 bp target sequence for each RNA species. Each of the target sequences was unique to spliced (i.e., exon1-exon2 junction) and pre-spliced (i.e., exon1-intron1 junction) mRNA from selected genes, plus abundant loading control RNAs (CEP170, EEF1A1 and RPL27, for which only mature mRNA species were counted). Counts for target RNAs were subtracted by background, which was determined by negative control target sequences not present in the human transcriptome. The counts were then normalized according to the abundant three control RNAs. To further improve the dataset, the minimal normalized counts were at least 2-fold of the maximal standard deviation. To control for sampling heterogeneity, two-tailed Dixon's Q outlier removal was performed with α=0.05. Finally, relative pre-mRNA level was calculated based on the equation below:

Relative pre-mRNA=pre-mRNA÷mRNA where "mRNA" and "pre-mRNA" represent the counts measured in the control or AD cases. To simplify the dataset, relative pre-mRNA level was normalized by setting the value in the controls to 100.

TaqMan quantitative RT-PCR was also used for analyzing transcripts. The pre- and mature mRNA levels are represented by the PCR products spanning exon1-intron1 and exon1-exon2 junctions, respectively. RNA samples of high quality were used (Mean $RIN_{Control}$=8.6, range 7.9-8.8; Mean $RIN_{AD}$=8.5, range 8.5-8.8). Total RNA (2 μg) was used for cDNA synthesis by High Capacity cDNA Reverse Transcription Kit (Life Technologies), followed by qRT-PCR in triplicate (Applied Biosystems 7500 Fast Real-Time PCR System). Multiplex reactions were performed with additional detection of the house-keeping gene TBP. RNA expression was calculated by the $2^{-\Delta\Delta C_T}$ method. See Livak & Schmittgen, Methods, 2001, 25(4):402-408. The relative pre-mRNA level was derived using the equation above.

Knockdown of U1-70K and Chemical Inhibition of RNA Splicing

U1-70K in HEK293 cells was knocked down by an equally mixed siRNA pool (Dharmacon, #05-GCCGUA-CAUUCGAGAGUUU (SEQ ID NO:1), #06-ACACGCA-GAUGGCAAGAAG (SEQ ID NO:2), #07-UACACAUG-GUCUACAGUAA (SEQ ID NO:3), #08-GAGAGUGAAUUAUGACACA (SEQ ID NO:4), with a non-targeting control #01-UGGUUUACAUGUCGACUAA (SEQ ID NO:5)) or individual siRNAs. The cells were cultured in DMEM media supplemented with 10% FBS (Life Technologies), transfected with 10 nM siRNA by Lipofectamine RNAiMax (Life technologies), incubated for two days, and then changed into a low serum medium (1% FBS) for a different period of time as indicated. The cells were harvested for Western blotting, while the medium was collected for Aβ40 ELISA assays (Millipore). For chemical inhibition analysis, cultured cells were treated with mock (DMSO) or isoginkgetin (HPLC purified, >98% purity, WuXi AppTec), incubated for indicated periods of time, and harvested for Western blotting and immunofluorescence analysis.

RT-PCR for Selected Transcripts in Cultured Cells

Total RNA (2 μg) was extracted by RNeasy Mini Kit (Qiagen) followed by cDNA synthesis by High Capacity cDNA Reverse Transcription Kit (Life Technologies) and PCR reactions. The PCR products were resolved by electrophoresis on 10% Novex polyacrylamide TBE-urea Gels (Life Technologies), and probed with SYBR Safe DNA Gel Stain (Life Technologies).

Differentiation of Neuroblastoma Cells and Human Embryonic Stem Cells

SH-SY5Y cells were cultured in DMEM-F12 (1:1) media supplemented with 2 mM L-glutamine and 10% FBS (Life Technologies), and differentiated. The cells were treated with 10 μM all-trans-retinoic acid (RA, Sigma) for 5 days, and then incubated in serum-free media supplemented with 10 μM RA and 50 ng/ml brain-derived neurotrophic factor (BDNF, Alomone Labs) for another 5 days.

Human embryonic stem cells (H9 line, P35 to P48) were maintained and differentiated. Colonies were lifted from the mouse fibroblast feeder layer and maintained in suspension culture as "embryoid bodies" (EBs) for 2 weeks in hES cell medium (Invitrogen, DMEM-F12, 5% Knock-out Serum Replacement, 1 mM L-glutamine, 1% MEM non-essential amino acids, and 0.1 mM 2-mercaptoethanol) supplemented daily with human recombinant basic-FGF (10 ng/ml, Peprotech). Resulting EBs were plated onto laminin (20 μg/ml, Cultrex, Trevigen) coated culture wells and allowed to develop into colonies showing neuroepithelial "rosettes". Rosettes colonies were then manually picked and cultured in NPC medium (Invitrogen, DMEM-F12, B27 and 1% Penicillin/Streptomycin) supplemented with basic-FGF. After 2 to 3 passages through manual picking to clean the culture from other types of cells, pure NPC colonies were induced to differentiate by replacing basic-FGF with BDNF and NT-3 (10 ng/ml each, Peprotech) for 8-12 weeks.

Identifying Spliceosome Components in Human Cerebral Spinal Fluid (CSF).

Figure 5:
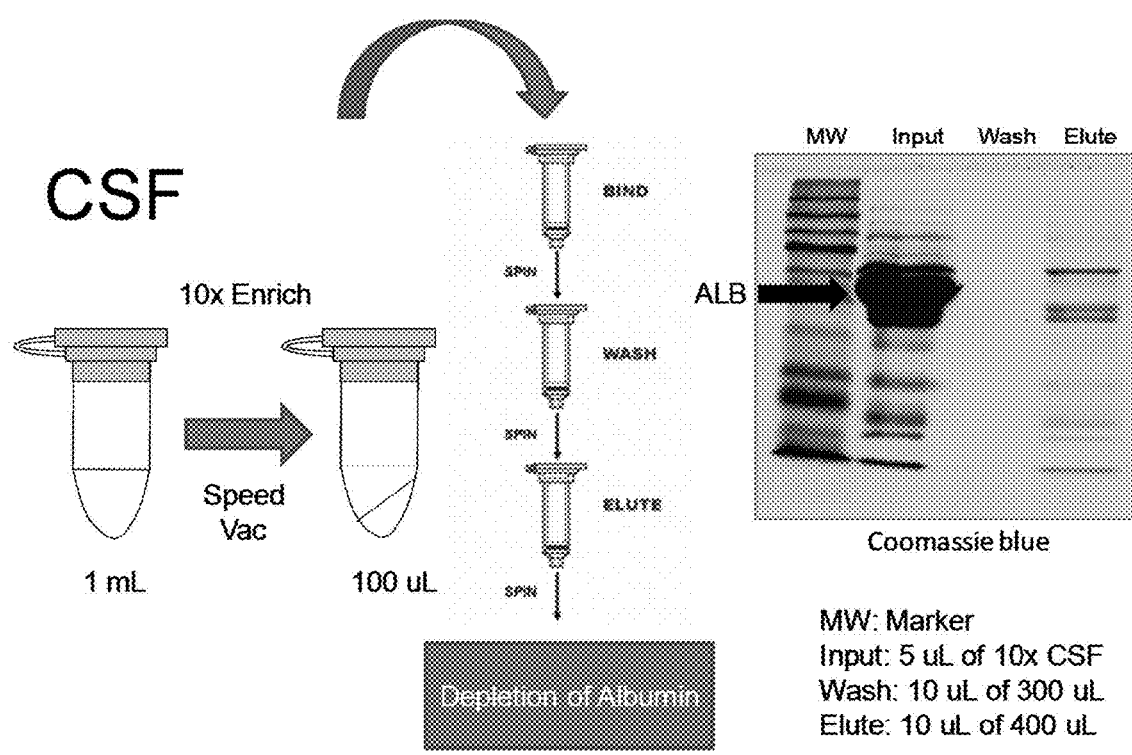
FIG. 5 shows data on experimental design for albumin depletion from human cerebral spinal fluid (CSF).

CSF is a source of U1 snRNPs. The large dynamic range of proteins in CSF makes mass spectrometry (MS) based proteomic analysis challenging because high-abundant proteins, such as albumin, will often mask those of lower abundance in the samples. Björhall et al., (2005) Proteomics 5, 307-317. To circumvent this limitation albumin depletion spin columns (Qiagen) are used to reduce the amount of albumin sequenced in MS proteomic experiments. Human CSF was tested. As shown in FIG. 5, a significant reduction of albumin (ALB) signal was determined to be reduced by SDS-PAGE following immuno-depletion (Elute), whereas other proteins remained. MS-based proteomic analysis of equal protein amounts of the non-depleted (input) and depleted (elute) CSF samples showed that greater than 95 percent of the ALB signal was reduced following this. Moreover, 1.7 times as many proteins were identified in the ALB depleted (n=2,734) versus non-depleted (n=1,619) samples. Notably 35 either core U1 snRNPs or associated members of the U1 spliceosome complex were identified from the ALB depleted samples. TP=total peptides, TSC=Total Spectral Counts, Reference-=NCBI RefSeq

TABLE 2

Spliceosome proteins identified in CSF after depletion

| Reference | TP | TSC | Description |
| --- | --- | --- | --- |
| NP_919223.1 | 5 | 6 | heterogeneous nuclear ribonucleoprotein A3 [Homo sapiens] |
| NP_114032.2 | 8 | 13 | heterogeneous nuclear ribonucleoprotein U isoform a [Homo sapiens] |
| NP_112533.1 | 8 | 17 | heterogeneous nuclear ribonucleoproteins A2/B1 isoform B1 [Homo sapiens] |
| NP_005372.2 | 7 | 10 | nucleolin [Homo sapiens] |
| NP_001348.2 | 7 | 12 | ATP-dependent RNA helicase A [Homo sapiens] |
| NP_005817.1 | 7 | 8 | heterogeneous nuclear ribonucleoprotein R isoform 2 [Homo sapiens] |

TABLE 2-continued

Spliceosome proteins identified in CSF after depletion

| Reference | TP | TSC | Description |
|---|---|---|---|
| NP_002131.2 | 7 | 12 | heterogeneous nuclear ribonucleoprotein K isoform a [*Homo sapiens*] |
| NP_054733.2 | 6 | 8 | U5 small nuclear ribonucleoprotein 200 kDa helicase [*Homo sapiens*] |
| NP_062543.1 | 1 | 4 | heterogeneous nuclear ribonucleoprotein H2 [*Homo sapiens*] |
| NP_001244222.1 | 5 | 9 | heterogeneous nuclear ribonucleoprotein H [*Homo sapiens*] |
| NP_004651.2 | 4 | 4 | ATP-dependent RNA helicase DDX3Y [*Homo sapiens*] |
| NP_005753.1 | 4 | 6 | transcription intermediary factor 1-beta [*Homo sapiens*] |
| NP_001460.1 | 4 | 5 | X-ray repair cross-complementing protein 6 [*Homo sapiens*] |
| NP_001609.2 | 4 | 4 | poly [ADP-ribose] polymerase 1 [*Homo sapiens*] |
| NP_005057.1 | 4 | 5 | splicing factor, proline- and glutamine-rich [*Homo sapiens*] |
| NP_001193929.1 | 4 | 7 | heterogeneous nuclear ribonucleoprotein D-like isoform b [*Homo sapiens*] |
| NP_002256.2 | 3 | 3 | importin subunit beta-1 [*Homo sapiens*] |
| NP_066964.1 | 3 | 3 | X-ray repair cross-complementing protein 5 [*Homo sapiens*] |
| NP_004387.1 | 3 | 3 | probable ATP-dependent RNA helicase DDX5 [*Homo sapiens*] |
| NP_006796.1 | 2 | 3 | heterogeneous nuclear ribonucleoprotein A0 [*Homo sapiens*] |
| NP_036558.3 | 2 | 2 | splicing factor 3B subunit 3 [*Homo sapiens*] |
| NP_004166.1 | 2 | 2 | small nuclear ribonucleoprotein Sm D3 [*Homo sapiens*] |
| NP_003008.1 | 2 | 4 | serine/arginine-rich splicing factor 3 [*Homo sapiens*] |
| NP_001012496.1 | 2 | 2 | splicing factor U2AF 65 kDa subunit isoform b [*Homo sapiens*] |
| NP_008855.1 | 2 | 2 | serine/arginine-rich splicing factor 1 isoform 1 [*Homo sapiens*] |
| NP_006616.1 | 2 | 2 | serine/arginine-rich splicing factor 10 isoform 1 [*Homo sapiens*] |
| NP_542781.3 | 2 | 2 | serine/arginine-rich splicing factor 12 [*Homo sapiens*] |
| NP_003087.1 | 1 | 1 | small nuclear ribonucleoprotein G [*Homo sapiens*] |
| NP_003085.1 | 1 | 1 | small nuclear ribonucleoprotein E [*Homo sapiens*] |
| NP_005617.2 | 1 | 1 | serine/arginine-rich splicing factor 4 [*Homo sapiens*] |
| NP_006266.2 | 1 | 1 | serine/arginine-rich splicing factor 6 [*Homo sapiens*] |
| NP_003082.1 | 1 | 2 | small nuclear ribonucleoprotein-associated proteins B and B' isoform B [*Homo sapiens*] |
| NP_004588.1 | 1 | 2 | small nuclear ribonucleoprotein Sm D2 isoform 1 [*Homo sapiens*] |
| NP_004584.1 | 1 | 3 | transformer-2 protein homolog beta isoform 1 [*Homo sapiens*] |
| NP_001245283.1 | 1 | 1 | 116 kDa U5 small nuclear ribonucleoprotein component isoform c [*Homo sapiens*] |

Ultrastructural and Biochemical Properties of U1-70K in AD Brain

The RNA-binding protein U1-70K and other core U1 small nuclear ribonucleoproteins (snRNPs) are sarkosyl-insoluble and form cytoplasmic tangle-like aggregates in AD brain. Although U1-70K can co-localize with tau in AD cortex by immunofluorescence at a cellular level, the precise sub-cellular localization and ultrastructural characterization of U1-70K in AD has not been defined. Immunogold transmission electron microscopy (EM) of AD cortical sections was performed, which revealed both nuclear and cytoplasmic U1-70K distribution within neurons (FIG. 6A). Notably, clusters of immunogold U1-70K particles in the cytoplasm were frequently concentrated around filamentous structures that resembled twisted-ribbon NFTs known to be comprised of hyperphospohrylated tau in terms of their periodicity and ultrastructural appearance. Immunogold EM with AT8 antibodies that detect phosphorylated tau (pSer202/pThr205) showed a similar distribution pattern. In the nucleus, a majority of snRNPs localize in interchromatin granule clusters and, consistently, clusters of immunogold U1-70K in the nucleus were typically found associated with dense chromatin structures (FIG. 6A). Neither AT8 nor U1-70K positive tangle-like structures were observed in the nucleus. These ultrastructural observations support immunohistochemical findings of U1-70K distribution into cytoplasmic tangle-like aggregates within neurons in AD cortex (FIG. 6B).

To confirm whether the biochemical properties of U1-70K supported the immunogold EM and immunohistochemical finding in AD cases, total brain homogenates were fractionated into sarkosyl-soluble and -insoluble fractions, respectively, and immunoblotted for U1-70K (FIG. 6C). Both AD and control cases had equivalent U1-70K levels in total homogenates prior to fractionation. However, following fractionation, U1-70K was nearly completely sarkosyl-soluble in controls, whereas in AD, U1-70K was nearly completely insoluble (FIG. 6C). The near complete sarkosyl insolubility observed for U1-70K in AD cortex is not consistent with the frequency of U1-70K cytoplasmic aggregates observed by immunohistochemistry, since the majority of U1-70K is localized to the nucleus as in control brains. Although a number of cells harbor cytoplasmic U1-70K tangles (FIG. 6C, black arrows), approximately 80-90% neuronal nuclei within the field have normal nuclear U1-70K with no obvious cytoplasmic aggregates. Moreover, glia show only the expected nuclear pattern of staining in AD and control cases. This observation was consistent across the AD cases examined. Thus, the near complete shift of U1-70K into the sarkosyl-insoluble fraction in AD brain cannot be attributed to the aggregated cytoplasmic pool of U1-70K alone (FIGS. 6A and B). Following AD tissue homogenization, aggregate prone U1-70K itself or other modifiers (i.e., aggregate prone tau or nucleic acids) sequester normal natively folded conformers of soluble U1-70K into insoluble aggregates.

AD Homogenates can Seed Both Soluble Control Brain and Recombinant U1-70K

Figure 8:
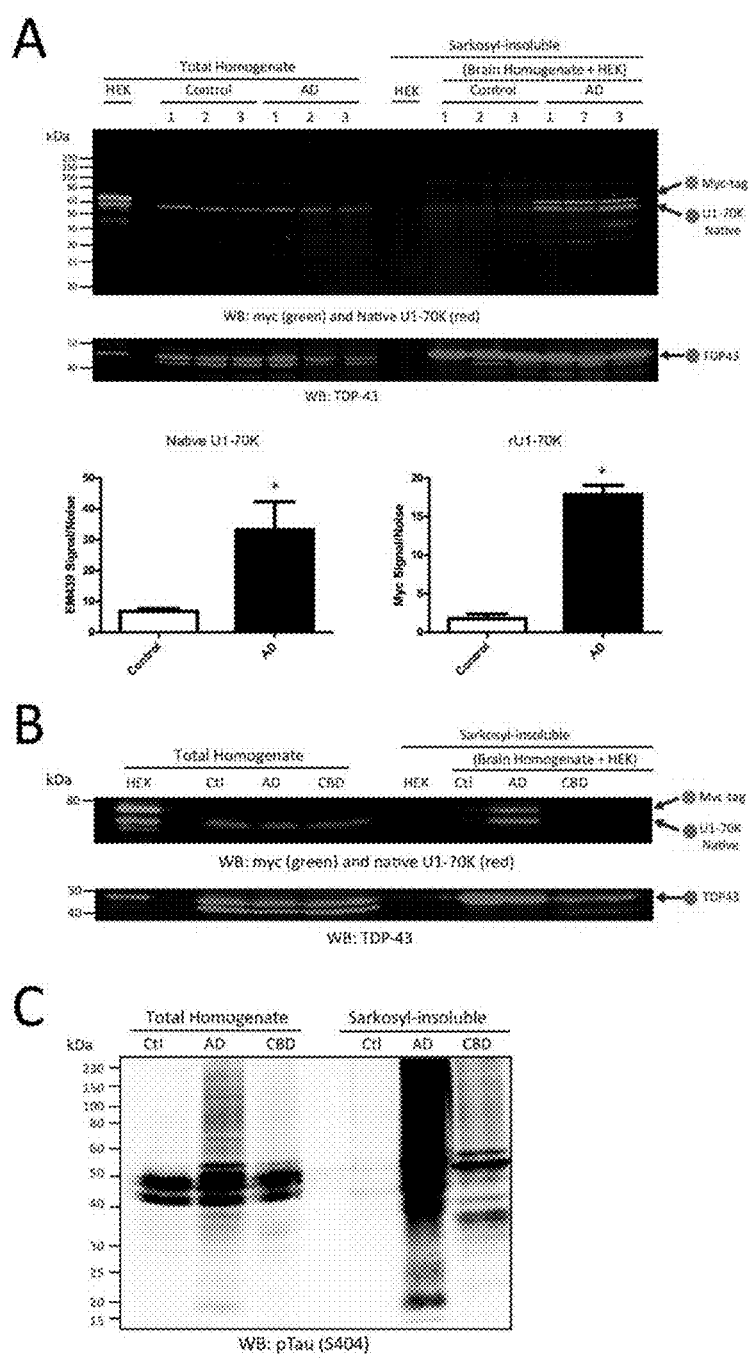
FIG. 8 shows data indicating AD homogenates can seed soluble recombinant U1-70K. HEK293T lysate (200 µg) expressing recombinant myc-tagged U1-70K (rU1-70K) was added to control (n=3) and AD (n=3) brain homogenates (5 mg) prior to fractionation (left panel). (A) The resulting sarkosyl-insoluble fractions were analyzed by quantitative western blotting for levels of U1-70K (right panel) (WB) using EM349 (red) for native U1-70K and Myc-tag (green) for rU1-70K. HEK lysate alone did not harbor insoluble rU1-70K. TDP-43 (red) served as a loading control (bottom panel). A significant increase of both native and rU1-70K was observed in the sarkosyl-insoluble AD fractions compared to control. Statistical significance (*) was calculated using Student's t-test ($p<0.05$). (B) Compared to AD homogenate, a CBD homogenate did not seed rU1-70K. TDP-43 served as a loading control (bottom panel). (C) Both CBD and, to a greater extent AD homogenate, had increased levels of sarkosyl-insoluble phosphorylated tau (pSer404) levels compared to control human brain homogenate.

To determine whether AD homogenates can seed or sequester normal soluble U1-70K, AD and control homogenates were mixed in six ratios with an increasing percent total AD homogenate, followed by the fractionation into sarkosyl-insoluble fractions (FIG. 7A-B), which were then analyzed by Western blotting for U1-70K. Western blot analysis of sarkosyl-insoluble U1-70K from the AD plus control homogenate mixture series demonstrated that U1-70K insolubility increased in a nonlinear, sigmoidal fashion (FIG. 7C). In contrast, Western blot analysis of sarkosyl-insoluble U1-70K from AD homogenate at the exact proportions added to control brain, yielded a clearly linear increase that was significantly different than the sigmoidal curve just described. In addition U1-70K in the control homogenate was entirely soluble in the absence of AD homogenate. Together, these results indicate that AD homogenate induces insolubility of control brain-derived U1-70K. The ability of AD homogenates to sequester soluble recombinant U1-70K into the insoluble fraction (hereafter referred to as seeding) was also assayed. HEK-293T cell lysate with over-expressed recombinant myc-tagged U1-70K (rU1-70K) was added to either AD or control brain homogenates followed by fractionation (FIG. 8A).

Although rU1-70K over-expressed in HEK293T cells and incubated at 4° C. for up to 12 hours is nearly completely sarkosyl-soluble, mixture with AD cortex homogenates under the same conditions induced insolubility of rU1-70K; whereas control brain homogenates did not. Notably, the levels of sarkosyl-insoluble rU1-70K correlated with native U1-70K insolubility in the same AD samples (FIG. 8A).

To confirm that the U1-70K seeding phenomenon was specific to AD, a seeding assay was performed with brain homogenates derived from an individual with corticobasal degeneration (CBD), a progressive neurological disorder that affects the basal ganglia and pre-frontal cortex and is neuropathologically characterized by the accumulation of hyperphosphorylated detergent-insoluble tau. Compared to the AD homogenate the CBD cortical homogenate was incapable of seeding rU1-70K expressed in HEK-293T cell lysate (FIG. 8B). Sarkosyl insoluble CBD fractions lacked both native and rU1-70K signal by Western blotting indicating that the seeding effect is not mediated by insoluble tau species in CBD (FIG. 8C), though this does not rule out the effect of tau species in AD that may drive the seeding effect. Regardless, this result is consistent with our previous findings that U1-70K aggregation is specific to AD and not other neurodegenerative diseases, including non-AD tauopathies. In sum, AD, but not CBD homogenates were effective at seeding both soluble U1-70K from control brain and rU1-70K expressed in HEK293 cells.

Seeding is Independent of RNA and is Abolished by Proteinase K Treatment

Figure 9:
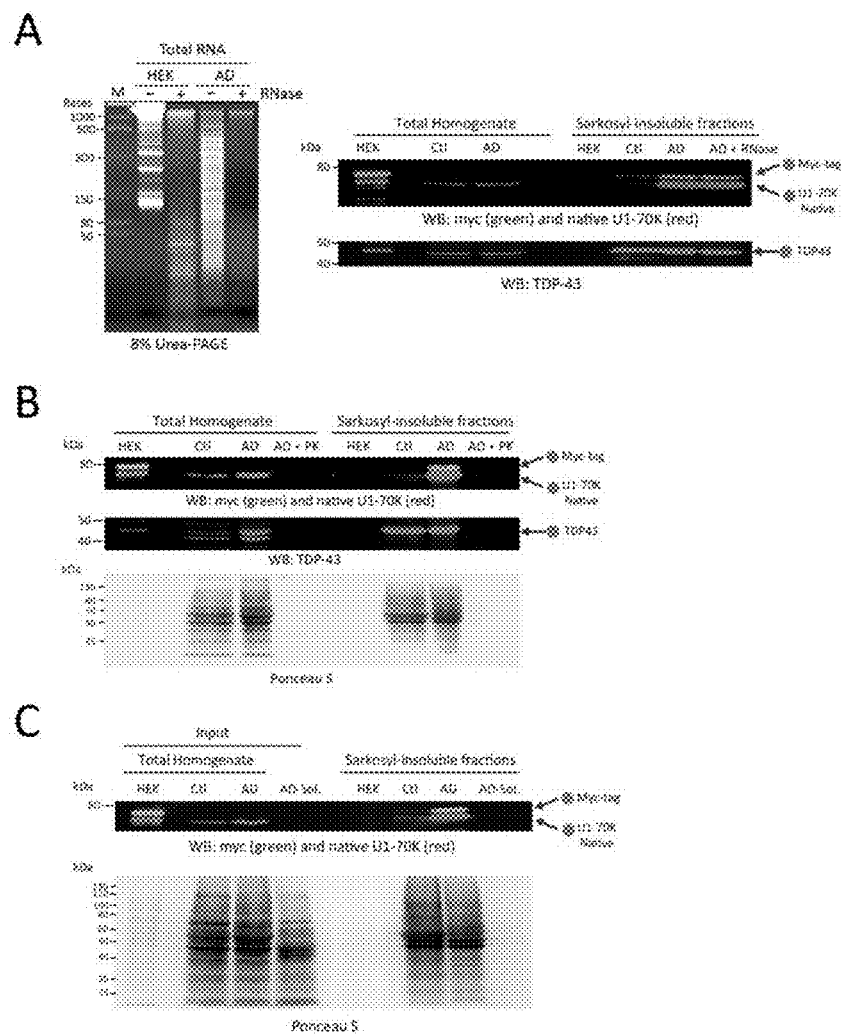
FIG. 9 shows data indicating U1-70K seeding is not dependent on RNA and requires pathologic aggregate prone proteins in AD homogenate (A) HEK293T lysate (200 µg) expressing recombinant Myc-tagged U1-70K (rU1-70K) and AD brain homogenate (5 mg) were pre-treated with RNAse A (200 µg/ml) to digest all RNA prior to seeding experiments (left panel). Total RNA was analyzed on an 8% Urea-PAGE gel following TRIzol extraction. A molecular weight marker (M) is also shown. HEK-293T lysates (200 µg) expressing myc-tagged U1-70K (rU1-70K) (+/−RNase treatment) were incubated alone, with control homogenate and AD homogenate (5 mg, +/−RNase treatment), incubated 4 hrs at 4° C. and fractionated. Western blot (WB) analysis of sarkosyl-insoluble fractions reveals equivalent seeding ability for native U1-70K (red) and rU1-70K (green) independent of RNA. (right panel). TDP-43 served as a loading control (bottom panel). (B) The protein-dependence of U1-70K seeding was assayed by digesting AD homogenate (5 mg) with proteinase K (200 µg/ml) for 1 hr at 37° C. After inhibition with PMSF, the PK-treated AD homogenate was incubated with HEK293T lysate expressing rU1-70K for 4 hrs at 4° C. and fractionated. Ponceau S staining of the membrane indicates near complete digestion of protein in the PK-treated samples (bottom panel). The ability of the PK-treated AD homogenate to seed rU1-70K was severely impaired relative to the untreated AD homogenate. (C) rU1-70K expressed in HEK293 cell lysate (200 µg) was added to 5 mg control homogenate, AD homogenate and sarkosyl-soluble AD fractions (AD sol.) incubated 4 hrs at 4° C. The samples were fractionated and the sarkosyl-insoluble fractions were subjected to WB analysis. Ponceau S staining of the transfer membrane prior to WB shows equal protein loading across total control homogenate, AD homogenate and sarkosyl-soluble AD fractions (bottom panel).

U1 snRNA co-aggregates with U1-70K in AD brain. Therefore, the U1 snRNA itself could serve as a necessary scaffold for the seeding of U1-70K aggregates in AD brain tissue. To determine whether RNA is required to seed soluble rU1-70K HEK-293T and AD brain homogenates were pre-treated both with RNase A prior to seeding assays (FIG. 9A). Urea-PAGE shows near complete degradation of intact RNA in both RNase-treated AD homogenates and HEK-293T homogenates that have over-expressed rU1-70K. Both RNase-treated and untreated AD brain homogenates were able to seed comparable levels of recombinant rU1-70K. Native levels of sarkosyl-insoluble U1-70K in AD were also unaffected by RNase treatment suggesting that U1-70K insolubility in AD is independent of RNA. To assess whether U1-70K seeding is protein directed, AD homogenate was pre-treated with proteinase K (PK) and assayed for the ability of PK treated homogenates to seed rU1-70K (FIG. 9B). Ponceau S staining of AD homogenate following PK treatment confirmed near complete protein degradation. Compared to untreated AD homogenate, the PK digested homogenates were incapable of seeding rU1-70K. Together, these data support that the observed U1-70K in AD brain homogenates does not require RNA, but rather is protein directed.

U1-70K Seeding Requires the Sarkosyl-Insoluble AD Proteome and does not Correlate with Tau Levels To determine if the aggregate-prone protein pool in AD is necessary for U1-70K seeding, the ability of sarkosyl-soluble AD fractions to seed rU1-70K was assessed (FIG. 9C). Unlike AD total homogenates the sarksoyl-soluble fractions were incapable of seeding rU1-70K, indicating that either misfolded U1-70K itself or other aggregated proteins in AD homogenates mediate this effect.

Figure 6:
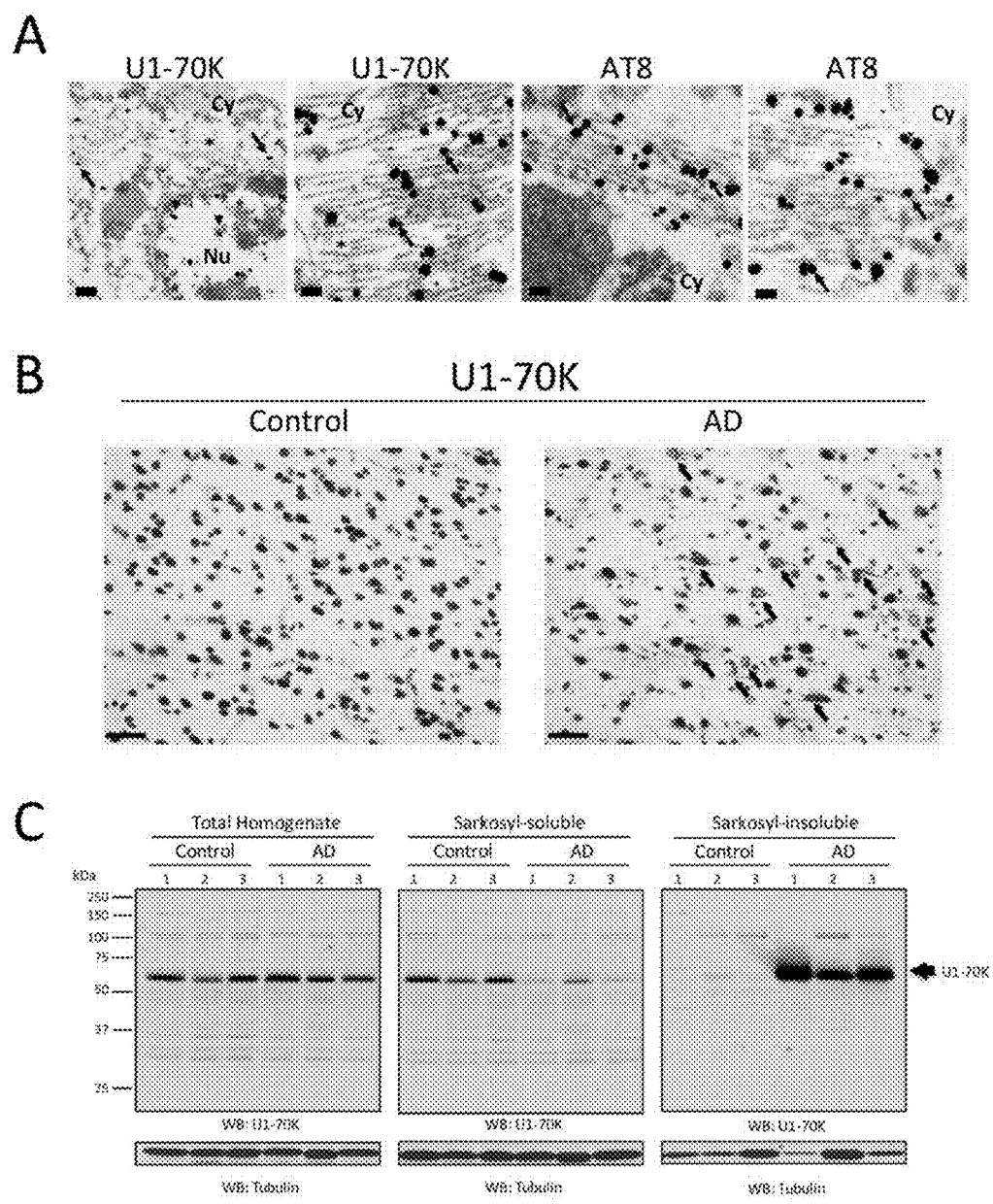
FIG. 6 shows data on the structural and biochemical properties of U1-70K in AD. (A) Immunogold electron microscopy of U1-70K and for comparison, tau (AT8) in AD frontal cortex. Immunogold positive staining for U1-70K (left panel) is observed in both the nucleus (Nu), denoted by arrow heads and cytoplasm (Cy), denoted by arrows. The asterisk denotes twisted-ribbon tangle-like structures positive for U1-70K, also shown at higher magnification. Scale bar is 1 μm (left) 100 μm (middle) 0.2 μm (right) (B) Immunohistochemisty using antibodies against U1-70K in both control and AD brain tissue. Arrows highlight cytoplasmic U1-70K tangles that are seen in AD but not control brains (Scale bar is 50 uM). (C) U1-70K displays a near complete solubility shift in AD brain. Total brain homogenates (TH) prepared from control (n=3) and AD (n=3) frontal cortex (left panel) were fractionated into sarkosyl-soluble (middle panel) and sarkosyl-insoluble fractions (right panel) and immunoblotted for U1-70K using EM439 polyclonal antibody.
Figure 10:
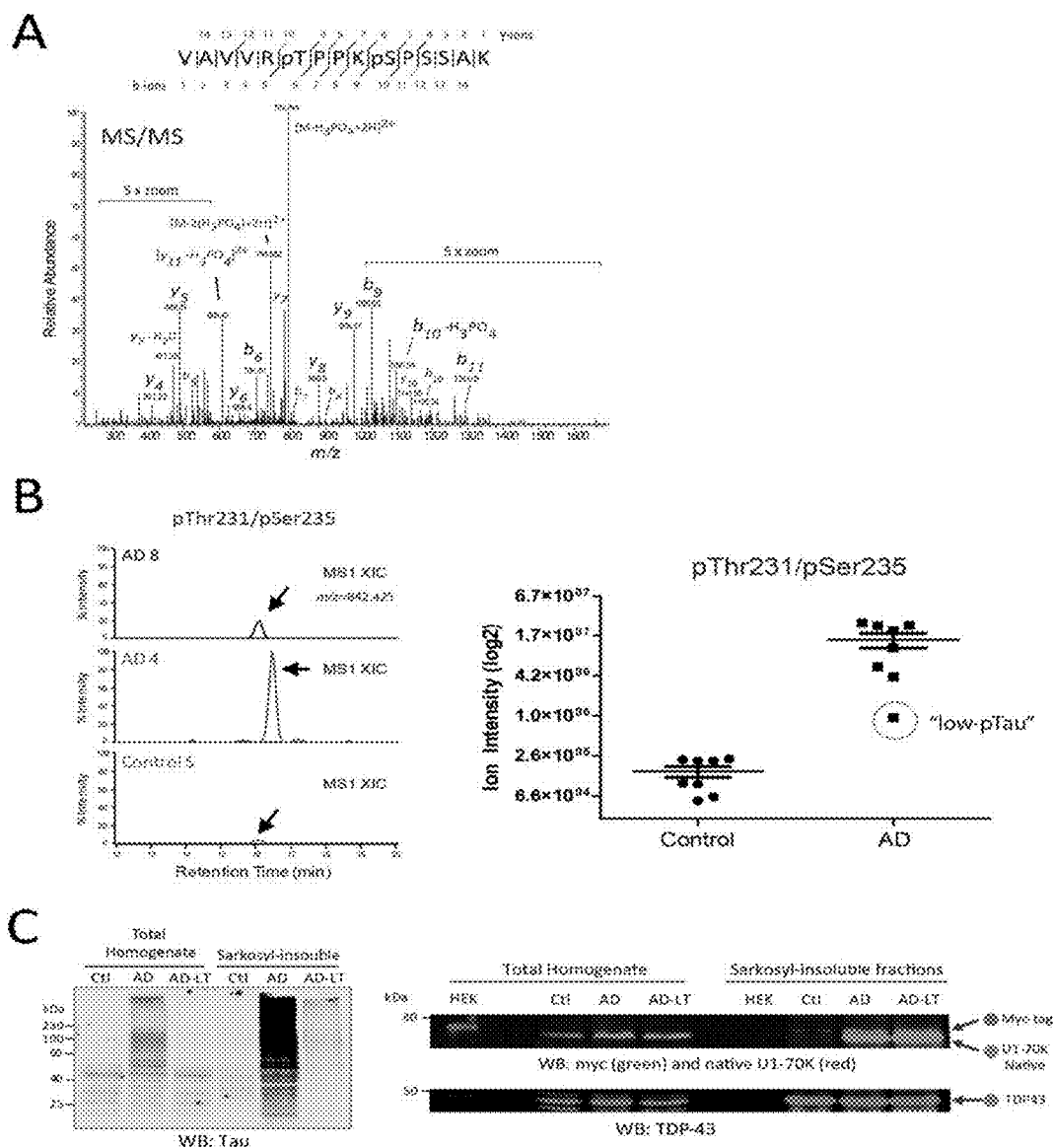
FIG. 10 shows data indication U1-70K seeding and aggregation does not correlate with phosphorylated tau levels in AD homogenates. Liquid chromatography coupled to tandem mass spectrometry (LC-MS/MS) was used to identify and quantify tau phosphopeptides in control and AD brain homogenates. Phospho-tau (pTau) peptides were identified by MS/MS and quantified by extracted ion chromatography (XIC) of full precursor MS1 scans. (A, left panel) Representative MS/MS spectrum for the pTau peptide mapping to modification sites on Thr231 and Ser235. (A, right panel) Representative extracted ion chromatogram (measured as the percentage intensity using a defined MS1 precursor m/z of 842.425) for the pT231/pS235 modified tau phosphopeptide was measured across a control and two AD cases. Peptide intensities were normalized to AD4. (B) A "low-pTau" AD case 8 (E04-172) had 17 fold less pT231/pS235 modified tau phosphopeptide signal intensitythan the average of all other AD cases (n=7) measured. (C, left panel) AD case E04-172 had significantly less sarkosyl-insoluble tau compared to a high pTau AD case. (C, right panel) HEK293T cell lysate (200 µg) expressing Myc tagged U1-70K (rU1-70K) was incubated alone, with control and AD homogenate with either high (AD) or low levels (AD-LT) of sarkosyl-insoluble tau (left panel) prior to fractionation and Western blot (WB) analysis for native (red) and recombinant U1-70K (green), respectively, in the sarkosyl-insoluble fraction (right panel). WB for TDP-43 (bottom panel) served as a loading control.

To assess whether the seeding phenomenon was directly dependent on the presence of endogenous U1-70K in AD brain homogenate, U1-70K from AD homogenates was deplete by immunoprecipitation. However, despite employing two separate commercially available antibodies in conjunction with magnetic and sepharose-based protein G resin, only about 5% of U1-70K was captured from AD homogenates, prepared in immunoprecipitation-compatible buffers (0.5% (v/v) NP-40 and sodium deoxycholate). The possibility that sarkosyl-insoluble tau in AD brain was responsible for seeding of rU1-70K was tested because i) both proteins are highly sarkosyl-insoluble in AD tissue; ii) U1-70K aggregates co-localize with tau in AD frontal cortex; and iii) both U1-70K and tau are ultrastructurally localized to paired helical filaments (FIG. 6). Quantitative mass spectrometry was used to identify potential AD cases with significantly lower levels of phosphorylated tau (pTau). Our phosphoproteomic screen of eight AD cases and eight controls revealed an AD case (E04-172), which had, on average, a 14-fold reduction in signal intensity for pTau specific peptides in frontal cortex compared to the average of other AD cases. Representative examples of phosphopeptide identification and quantification by LC-MS/MS are provided in FIG. 10 A-B. It should be noted that this "low-pTau" AD case E04-172 had 9- and 6-fold higher levels of the pT231/pS235 and pS396/pS400/pT403 tau phosphopeptide signal intensity than the average of all controls (n=8). AD case E04-172 was classified as Braak stage 5, and described as having only moderate levels of NFTs in the prefrontal cortex after neuropathological examination, whereas other AD cases analyzed by LC-MS/MS were described as having severe levels of NFTs.

Consistent with the above phosphoproteomic signature measured by mass spectrometry the low-pTau AD individual had significantly less sarkosyl-insoluble tau compared to a high pTau AD case (FIG. 10C). However, both high and low tau AD cases had comparable levels of endogenoussarkosyl-insoluble U1-70K and both were equally effective at seeding soluble rU1-70K expressed in HEK293T cells (FIG. 10C). This result indicates that both U1-70K aggregation and seeding propensity in AD do not correlate with aggregated pTau levels or NFT burden in the brain, although it does not rule out a sub-stoichiometric effect of pTau on seeding of U1-70K.

The Intrinsically Disordered C-Terminus is Associated with U1-70K Seeding

Figure 11:
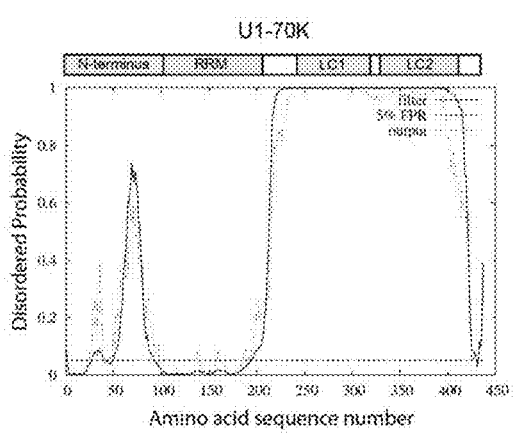
FIG. 11 shows data indicating the intrinsically disordered C-terminus is necessary for U1-70K seeding. (A) The DISOPRED algorithm predicts intrinsically disordered regions within the N-terminal (amino acids 50-100) and C-terminal (amino acids 220-437) portion of human U1-70K, which harbors two distinct low complexity domains, LC1 (amino acids 231-308) and LC2 (amino acids 317-407). (B) To determine which region(s) or amino acid sequences of U1-70K are required for seeding we assessed the ability of AD brain homogenate to seed GST-rU1-70K and a number of N- and C-terminal truncated fragments. Each GST-rU1-70K construct was expressed in HEK-293T cells (left panel) and individual lysates (200 µg) harboring equivalent amounts of recombinant protein were added to AD brain homogenate (left panel, last lane) and incubated for 12 hrs at 4° C. prior to fractionation. The sarkosyl-insoluble fractions (right panel) were subjected to WB analysis using anti-Myc-tag antibodies (green) for GST-rU1-70K and EM439 antibodies (red) for native U1-70K.
Figure 11:
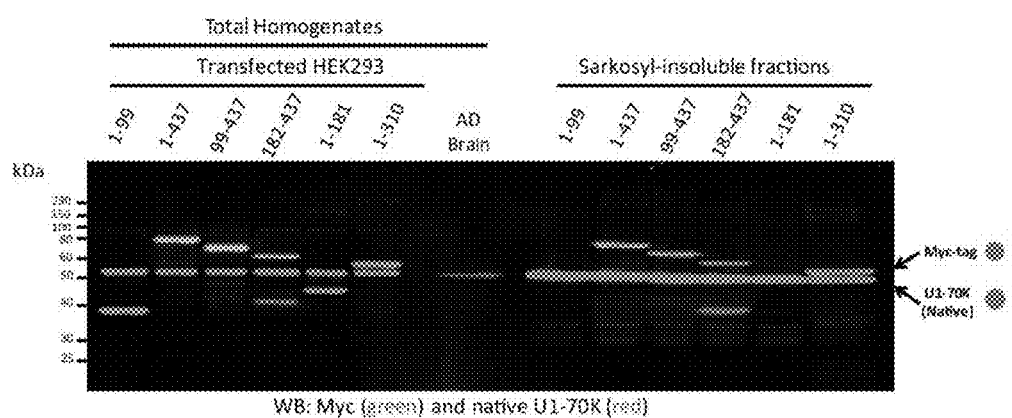

Several RNA binding proteins, including TDP-43, FUS, hnRNPA1 and ataxinA2 harbor low complexity (LC) domains that promote the formation of amyloid-like aggregates in other neurodegenerative diseases. U1-70K harbors two such domains, LC1 (amino acids 231-308) and LC2 (amino acids 317-407), which together comprise a majority of the C-terminal primary sequence. The DISOPRED algorithm predicts intrinsically disordered regions within the N-terminal (amino acids 50-100) and C-terminal (amino acids 220-437) regions of the protein (FIG. 11A). The C-terminal region is almost completely disordered as a consequence of the low amino acid complexity of LC1 and LC2. To determine which region(s) of the U1-70K primary sequence are required for seeding, the ability was assessed of AD brain homogenate to sequester GST-tagged full-length rU1-70K as well as a number of N- and C-terminal truncated fragments likewise tagged (FIG. 11B).

A table with plasmids is provided below.

| Name | Vector | Sequence | Restriction Sites | Tags |
|---|---|---|---|---|
| U1-70K Full-length | pcDNA3.1 | 1-437 | HindIII/BamHI | C-terminal: Myc/DDK |
| GST-U1-70K Full-length | pLEXM-GST | 1-437 | EcoRV/XhoI | N-terminal: GST C-terminal: Myc/DDK |
| GST-U1-70K 1-99 | pLEXM-GST | 1-99 | EcoRV/XhoI | N-terminal: GST C-terminal: Myc/DDK |
| GST-U1-70K 1-181 | pLEXM-GST | 1-181 | EcoRV/XhoI | N-terminal: GST C-terminal: Myc/DDK |
| GST-U1-70K 1-310 | pLEXM-GST | 1-310 | EcoRV/XhoI | N-terminal: GST C-terminal: Myc/DDK |
| GST-U1-70K 182-437 | pLEXM-GST | 182-437 | EcoRV/XhoI | N-terminal: GST C-terminal: Myc/DDK |
| GST-U1-70K 99-437 | pLEXM-GST | 99-437 | EcoRV/XhoI | N-terminal: GST C-terminal: Myc/DDK |

Western blot analysis for GST-rU1-70K in the sarkosyl-insoluble AD fractions demonstrate that N-terminal fragments (1-99 and 1-181) had negligible signal compared to full-length or C-terminal fragments containing the LC domains. Of note, any protein construct containing the LC1 domain (amino acids 231-308) was sufficient for seeding by the AD homogenate.

AD brain homogenate containing insoluble U1-70K aggregates and with a variable burden of classical neurofibrillary tangles (i.e., paired helical filaments), can induce the aggregation of endogenous soluble U1-70K from control brain homogenate or recombinant U1-70K and render it sarkosyl-insoluble. The mechanisms that underlie this phenomenon appear to be RNA independent and require the presence of the sarkosyl-insoluble protein fraction of AD including U1-70K. Interestingly, our data do not appear to establish a correlation between pTau expression levels and the extent of U1-70K seeding ability. Finally, by expressing both N- and C-terminally truncated fragments of rU1-70K it was determined that any protein construct containing the LC1 domain (amino acids 231-308) was sufficient for seeding by the AD homogenate. Similar LC domains found in a variety of RNA binding proteins including the ALS associated FUS, TDP-43 and hnRNPA1, form amyloid-like fibers in disease and have been shown to aggregate in a (template-directed) prion-like manner in neurodegenerative disease (19, 37, 38). Taken together our data provides preliminary support for a similar aggregation mechanism for U1-70K in AD brain.

In certain embodiments, the disclosure relates to recombinant U1-70K optionally conjugated to a detectable marker. In certain embodiments, the disclosure relates to a nucleic acid that encodes a recombinant U1-70K optionally conjugated to a detectable marker wherein the nucleic acid further encodes a selectable marker, e.g., a gene which encodes an enzymatic activity that confers resistance to an antibiotic or drug upon the cell in which the selectable marker is expressed. In certain embodiments, detectable marker is a fluorescent protein. After recombinant production recombinant proteins can be further modified with detectable markers such as fluorescent dye, antibody epitope, biotin, ligand, steroid, quantum dot. In certain embodiments, the disclosure contemplates recombinant vectors and expression systems comprising these nucleic acids encoding a recombinant U1-70K.

Contemplated labels or other detectable moieties may have one or more physical properties that facilitate detection and possibly isolation of the recombinant proteins. In certain embodiments, the marker is a fluorescent protein, fluorescent dye, antibody epitope, biotin, ligand, steroid, quantum dot. Useful physical properties include a characteristic electromagnetic spectral property such as emission or absorbance, magnetism, electron spin resonance, electrical capacitance, dielectric constant or electrical conductivity. The marker may be ferromagnetic, paramagnetic, diamagnetic, luminescent, electrochemiluminescent, fluorescent, phosphorescent, chromatic or have a distinctive mass. Fluorescent moieties which are useful as markers include dansyl fluorophores, coumarins and coumarin derivatives, fluorescent acridinium moieties and benzopyrene based fluorophores and quantum dots. In addition to fluorescent markers, a variety of markers possessing other specific physical properties can be used to detect recombinant protein production. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity, positron emission tomography, and nuclear magnetic resonances and use of a mass spectrometer to detect presence of a marker with a specific molecular mass.

The invention claimed is:

1. A method of recording expression of U1-70K (U1 small nuclear ribonucleoprotein 70 kDa) in a sample from a subject suspected of having Alzheimer's disease, said method comprising the steps of:
   extracting U1-70K from brain tissue of the subject in an aqueous solution comprising a detergent providing a detergent soluble fraction and a detergent insoluble fraction,
   measuring increased expression of human U1-70K in the detergent insoluble fraction when compared to a control, and
   recording the increased expression on a computer readable medium.

2. The method of claim 1, wherein the detergent is N-lauroyl-sarcosine.

3. The method of claim 1, wherein the increased expression is evaluated by purifying U1-70K by a chromatography method and measuring an amount of U1-70K in the sample by mass spectrometry.

4. The method of claim 3, wherein the chromatography method is electrophoresis on a sodium dodecyl sulfate polyacrylamide gel or liquid chromatography.

5. The method of claim 1, wherein the increased expression is evaluated by measuring an amount of U1-70K in the sample by an affinity marker or affinity chromatography.

6. The method of claim 1, wherein the increased expression is measured by immunohistochemistry.

7. The method of claim 1, wherein the control is a sample from a subject that is normal.

8. The method of claim 1, wherein the control is a sample from a subject that is not diagnosed with Alzheimer's disease.

9. The method of claim 1, wherein the control is a sample from a subject without dementia.

* * * * *